(12) United States Patent
Nicholson et al.

(10) Patent No.: US 11,369,392 B2
(45) Date of Patent: Jun. 28, 2022

(54) INTRAVASCULAR CATHETER WITH FLUOROSCOPICALLY VISIBLE INDICIUM OF ROTATIONAL ORIENTATION

(71) Applicant: Traverse Vascular, Inc., Solana Beach, CA (US)

(72) Inventors: Bill Nicholson, York, PA (US); Brad Klos, Solana Beach, CA (US); Steve Howard, La Jolla, CA (US); David Matsuura, Solana Beach, CA (US)

(73) Assignee: TRAVERSE VASCULAR, INC., Solana Beach, CA (US)

( * ) Notice: Subject to any disclaimer, the term of this patent is extended or adjusted under 35 U.S.C. 154(b) by 251 days.

(21) Appl. No.: 16/838,782

(22) Filed: Apr. 2, 2020

(65) Prior Publication Data
US 2020/0330731 A1    Oct. 22, 2020

Related U.S. Application Data

(60) Provisional application No. 62/907,299, filed on Sep. 27, 2019, provisional application No. 62/830,199, filed on Apr. 5, 2019.

(51) Int. Cl.
*A61M 25/00* (2006.01)
*A61B 17/22* (2006.01)
(Continued)

(52) U.S. Cl.
CPC ............. *A61B 17/22* (2013.01); *A61F 2/82* (2013.01); *A61F 2/958* (2013.01); *A61M 25/007* (2013.01);
(Continued)

(58) Field of Classification Search
CPC .......... A61M 25/0052; A61M 25/0053; A61M 25/007; A61M 25/0108; A61M 25/0194;
(Continued)

(56) References Cited

U.S. PATENT DOCUMENTS 1,065,018 A   6/1913  Barber
1,383,683 A   7/1921  William
(Continued)

FOREIGN PATENT DOCUMENTS

CN    107260252 A  * 10/2017  ....... A61B 17/12172
DE       19634866      3/1998
(Continued)

OTHER PUBLICATIONS

International Search Report for International Application No. PCT/US20/26360 dated Jun. 25, 2020.

*Primary Examiner* — Nathan R Price
*Assistant Examiner* — Adam J. Cermak
(74) *Attorney, Agent, or Firm* — Knobbe Martens Olson & Bear LLP

(57) ABSTRACT

Intravascular catheters with fluoroscopically visible indicium of rotational orientation. The catheter includes an elongate flexible tubular body, having a proximal end, a distal end and a tubular side wall defining at least one lumen extending therethrough. At least first and second opposing pairs of radiopaque rings are embedded in the side wall, spaced axially apart from each other. A first transverse axis extending through the first pair of rings is rotationally offset from a second transverse axis extending through the second pair of rings. The rings may be supported by a subassembly integrated into the wall of the catheter. The subassembly may include a tubular body having a plurality of aperture portions connected by intervening hinge portions. In one implementation, the catheter is a reentry catheter.

15 Claims, 21 Drawing Sheets

(51) Int. Cl.
　　　*A61F 2/958*　　　(2013.01)
　　　*A61M 25/01*　　　(2006.01)
　　　*A61F 2/82*　　　(2013.01)
　　　*A61M 25/09*　　　(2006.01)

(52) U.S. Cl.
　　　CPC .... *A61M 25/0052* (2013.01); *A61M 25/0053* (2013.01); *A61M 25/0108* (2013.01); *A61M 25/0194* (2013.01); *A61B 2017/22002* (2013.01); *A61B 2017/22038* (2013.01); *A61B 2017/22071* (2013.01); *A61B 2017/22079* (2013.01); *A61B 2017/22095* (2013.01); *A61M 2025/09166* (2013.01)

(58) Field of Classification Search
　　　CPC ......... A61M 2025/09166; A61M 2025/09133; A61M 2025/0197; A61B 2017/22095
　　　See application file for complete search history.

(56) References Cited

U.S. PATENT DOCUMENTS

| | | | |
|---|---|---|---|
| 3,394,705 A | 7/1968 | Abramson et al. | |
| 4,771,949 A | 9/1988 | Behr et al. | |
| 5,221,256 A | 6/1993 | Mahurkar | |
| 5,419,777 A | 5/1995 | Hofling | |
| 5,464,395 A | 11/1995 | Faxon et al. | |
| 5,536,261 A | 7/1996 | Stevens | |
| 5,738,649 A * | 4/1998 | Macoviak | A61M 25/0068 604/107 |
| 5,769,828 A * | 6/1998 | Jonkman | A61M 25/0012 604/508 |
| 5,800,407 A * | 9/1998 | Eldor | A61M 25/007 604/264 |
| 6,161,543 A | 12/2000 | Cox | |
| 6,231,546 B1 * | 5/2001 | Milo | A61B 17/3207 600/585 |
| 6,480,747 B2 | 11/2002 | Schmidt | |
| 6,514,217 B1 | 2/2003 | Selmon et al. | |
| 6,579,311 B1 * | 6/2003 | Makower | A61B 1/3137 604/8 |
| 6,605,061 B2 | 8/2003 | Vantassel et al. | |
| 6,719,725 B2 | 4/2004 | Milo et al. | |
| 6,733,489 B2 | 5/2004 | Nutting et al. | |
| 7,134,438 B2 | 11/2006 | Makower et al. | |
| 7,191,015 B2 | 3/2007 | Lamson et al. | |
| 7,229,429 B2 | 6/2007 | Martin et al. | |
| 7,344,518 B2 * | 3/2008 | McGuckin, Jr | A61B 18/00 604/164.01 |
| 7,396,354 B2 | 7/2008 | Rychnovsky et al. | |
| 7,632,241 B2 * | 12/2009 | Raijman | A61M 25/0021 604/43 |
| 7,938,795 B2 | 5/2011 | Difiore et al. | |
| 8,075,580 B2 * | 12/2011 | Makower | A61B 1/3137 606/191 |
| 8,105,259 B2 | 1/2012 | Michishita | |
| 8,192,403 B1 | 6/2012 | Pursley | |
| 8,202,246 B2 | 6/2012 | Kugler et al. | |
| 8,295,947 B2 | 10/2012 | Lamson et al. | |
| 8,374,680 B2 | 2/2013 | Thompson | |
| 8,512,310 B2 | 8/2013 | Kugler et al. | |
| 8,834,448 B1 | 9/2014 | Pursley | |
| 8,920,449 B2 | 12/2014 | Wilkinson | |
| 9,095,648 B2 | 8/2015 | Kassab et al. | |
| 9,233,224 B1 | 1/2016 | Pursley | |
| 9,259,340 B2 | 2/2016 | Heuser et al. | |
| 9,301,774 B2 * | 4/2016 | O'Day | A61B 17/3478 |
| 9,486,239 B2 | 11/2016 | Anderson et al. | |
| 9,867,530 B2 | 1/2018 | Pursley | |
| 9,872,685 B2 | 1/2018 | Kugler et al. | |
| 9,878,128 B2 * | 1/2018 | Kugler | A61B 17/2256 |
| 10,065,018 B2 | 9/2018 | Rocha-Singh et al. | |
| 10,070,877 B2 | 9/2018 | Warren | |
| 10,117,659 B2 | 11/2018 | Zhou et al. | |
| 10,172,632 B2 | 1/2019 | Morero et al. | |
| 10,226,602 B1 | 3/2019 | Panian | |
| 10,226,603 B1 | 3/2019 | Panian | |
| 10,265,206 B2 | 4/2019 | Heuser et al. | |
| 10,335,174 B2 | 7/2019 | Wilkinson | |
| 10,456,252 B2 | 10/2019 | Simon et al. | |
| 10,456,557 B2 * | 10/2019 | Guala | A61B 17/22 |
| 10,603,467 B2 | 3/2020 | Alvarez et al. | |
| 10,610,669 B2 | 4/2020 | Rocha-Singh et al. | |
| 10,682,502 B2 | 6/2020 | Panian | |
| 10,722,252 B2 | 7/2020 | Brenizer et al. | |
| 10,806,474 B2 | 10/2020 | Kugler et al. | |
| 10,806,487 B2 * | 10/2020 | Kugler | A61B 17/3403 |
| 10,857,329 B2 | 12/2020 | Davies et al. | |
| 10,864,041 B2 | 12/2020 | Urbanski et al. | |
| 10,939,928 B2 | 3/2021 | Kugler et al. | |
| 10,980,552 B2 | 4/2021 | Mustapha | |
| 11,033,286 B2 | 6/2021 | Anderson | |
| 11,065,002 B2 | 7/2021 | Kugler et al. | |
| 11,154,312 B2 | 10/2021 | Nicholson et al. | |
| 2001/0016729 A1 | 8/2001 | Divino et al. | |
| 2002/0169436 A1 | 11/2002 | Gurm et al. | |
| 2003/0045842 A1 * | 3/2003 | Kawakita | A61M 25/007 604/264 |
| 2004/0133158 A1 | 7/2004 | Keith et al. | |
| 2008/0154172 A1 | 6/2008 | Mauch | |
| 2009/0043372 A1 * | 2/2009 | Northrop | A61M 25/0013 623/1.15 |
| 2009/0112153 A1 * | 4/2009 | Gregersen | A61M 1/3653 604/43 |
| 2009/0177119 A1 * | 7/2009 | Heidner | A61M 25/09 600/585 |
| 2010/0063479 A1 * | 3/2010 | Merdan | A61M 25/09 604/528 |
| 2010/0063534 A1 | 3/2010 | Kugler | |
| 2010/0076404 A1 * | 3/2010 | Ring | A61M 25/007 604/523 |
| 2011/0054448 A1 | 3/2011 | Bourne et al. | |
| 2011/0224666 A1 | 9/2011 | Davies et al. | |
| 2012/0179144 A1 * | 7/2012 | Carleo | A61M 25/0111 604/544 |
| 2013/0072957 A1 | 3/2013 | Anderson | |
| 2013/0197353 A1 * | 8/2013 | Von Oepen | A61M 25/0009 600/424 |
| 2013/0245430 A1 | 9/2013 | Selmon | |
| 2013/0304108 A1 | 11/2013 | Weber et al. | |
| 2014/0074108 A1 | 3/2014 | Warren | |
| 2014/0228876 A1 * | 8/2014 | Copeta | A61B 17/22 606/194 |
| 2015/0112374 A1 | 4/2015 | Wilkinson | |
| 2015/0174371 A1 | 6/2015 | Schaeffer et al. | |
| 2016/0074627 A1 | 3/2016 | Cottone | |
| 2017/0020563 A1 | 1/2017 | Anderson et al. | |
| 2017/0021127 A1 * | 1/2017 | Manouchehr | A61M 5/3291 |
| 2017/0100141 A1 * | 4/2017 | Morero | A61B 17/3478 |
| 2017/0281909 A1 * | 10/2017 | Northrop | A61M 25/0013 |
| 2018/0036021 A1 | 2/2018 | Kassab | |
| 2018/0056045 A1 | 3/2018 | Donoghue et al. | |
| 2018/0110525 A1 | 4/2018 | Kugler et al. | |
| 2018/0333162 A1 | 11/2018 | Saab | |
| 2018/0369539 A1 | 12/2018 | Rocha-Singh et al. | |
| 2019/0321059 A1 | 10/2019 | Takahashi et al. | |
| 2019/0357893 A1 * | 11/2019 | Weber | A61B 17/3468 |
| 2020/0015966 A1 | 1/2020 | Kiersey et al. | |
| 2020/0046944 A1 | 2/2020 | Cottone | |
| 2020/0060718 A1 * | 2/2020 | Patel | A61B 5/6852 |
| 2020/0078571 A1 * | 3/2020 | Kirt | A61M 25/005 |
| 2020/0315639 A1 | 4/2020 | Nicholson et al. | |
| 2020/0147347 A1 * | 5/2020 | Cottone | A61M 25/0194 |
| 2020/0230357 A1 * | 7/2020 | Fitzgerald | A61L 29/085 |
| 2020/0246596 A1 | 8/2020 | Panian | |
| 2021/0045757 A1 * | 2/2021 | Bouasaysy | A61B 17/22 |
| 2021/0153882 A1 | 5/2021 | Kugler et al. | |
| 2021/0162184 A1 * | 6/2021 | Lippert | A61L 31/022 |
| 2021/0338975 A1 * | 11/2021 | Cottone | A61M 25/0045 |
| 2021/0346656 A1 * | 11/2021 | Lippert | A61M 25/09041 |

(56) References Cited

U.S. PATENT DOCUMENTS

FOREIGN PATENT DOCUMENTS

| | | | | |
|---|---|---|---|---|
| DE | 102018119605 A1 * | 2/2020 | ........... | A61L 29/041 |
| JP | H10165508 | 6/1998 | | |
| JP | H10165508 A * | 6/1998 | ........... | A61M 25/00 |
| JP | H10165508 A | 6/1998 | | |
| WO | WO-0134237 A1 * | 5/2001 | .......... | A61M 25/007 |
| WO | WO-0170133 A2 * | 9/2001 | ............. | A61F 2/064 |
| WO | WO 2006/046244 | 5/2006 | | |
| WO | WO-2008024597 A2 * | 2/2008 | ...... | A61M 25/09033 |
| WO | WO-2009100129 A2 * | 8/2009 | ........ | A61B 17/3478 |
| WO | WO-2012068273 A1 * | 5/2012 | ..... | A61B 17/320725 |
| WO | WO-2012158152 A1 * | 11/2012 | ....... | A61B 17/12172 |
| WO | WO-2013003757 A2 * | 1/2013 | .......... | A61M 25/003 |
| WO | WO-2017175531 A1 * | 10/2017 | .......... | A61M 1/1698 |
| WO | WO 2018/165277 | 9/2018 | | |
| WO | WO-2019005903 A1 * | 1/2019 | ........ | A61M 25/0105 |
| WO | WO 2019/209798 | 10/2019 | | |
| WO | WO 2020/076833 | 4/2020 | | |
| WO | WO 2021/014316 | 1/2021 | | |
| WO | WO-2021021368 A1 * | 2/2021 | ........... | A61F 2/2436 |
| WO | WO 2021/084460 | 5/2021 | | |
| WO | WO 2021/084462 | 5/2021 | | |
| WO | WO 2021/086903 | 5/2021 | | |
| WO | WO-2021163635 A1 * | 8/2021 | ........ | A61M 25/0052 |

\* cited by examiner

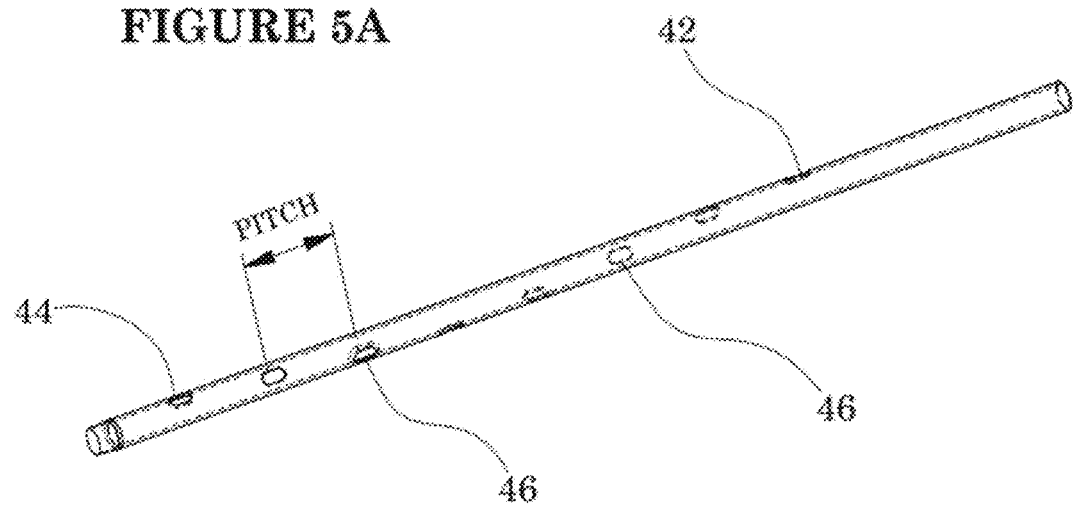
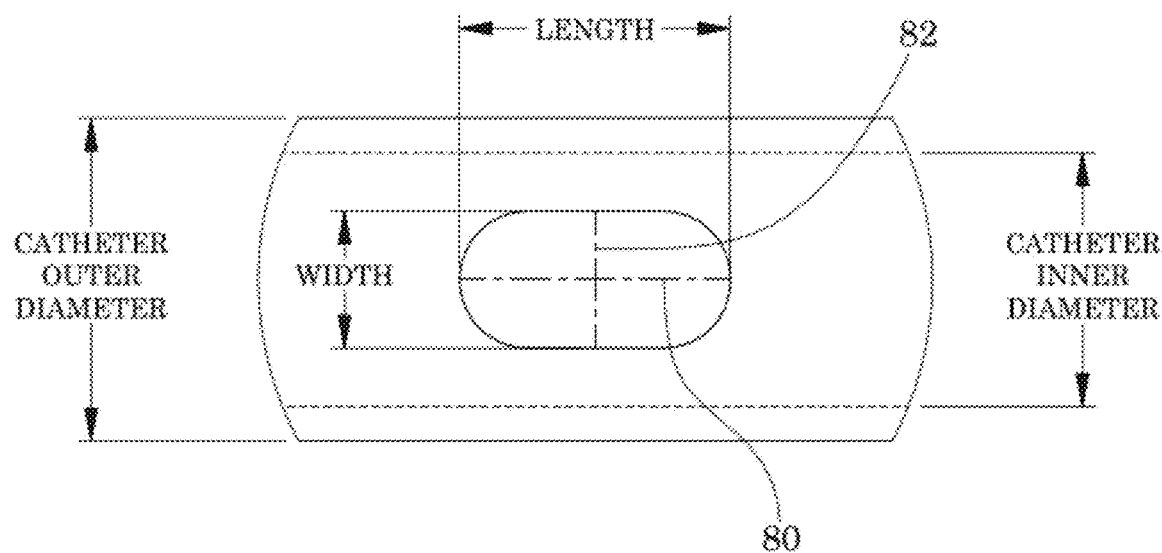

FIGURE 14
Visualization Under Fluoroscopy
- The catheter tip and/or shaft may be made of RO material for enhanced visualization under fluoroscopy
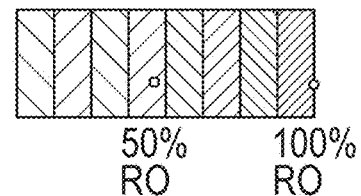
50% RO   100% RO
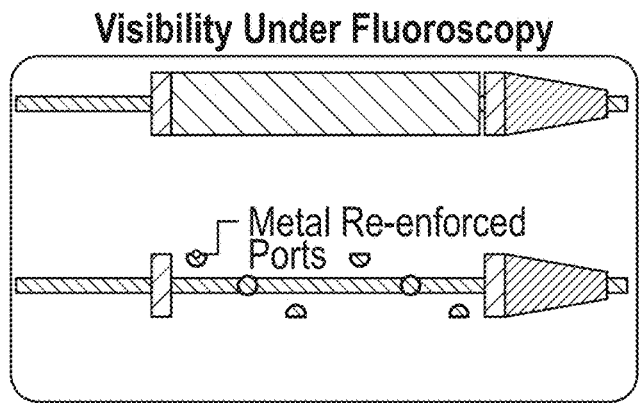
Cofiguration 1:
- Tapered Tip: 100% RO
- Guidewire: 80% RO
- Marker Bands: 60-70% RO
- Landing Zone: 50%
Cofiguration 2:
- Tapered Tip: 100% RO
- Guidewire: 80% RO
- Marker Bands: 60-70% RO
- Landing Zone: Radiolucent
- Ports: 50% Metal Re-enforced
FIGURE 15
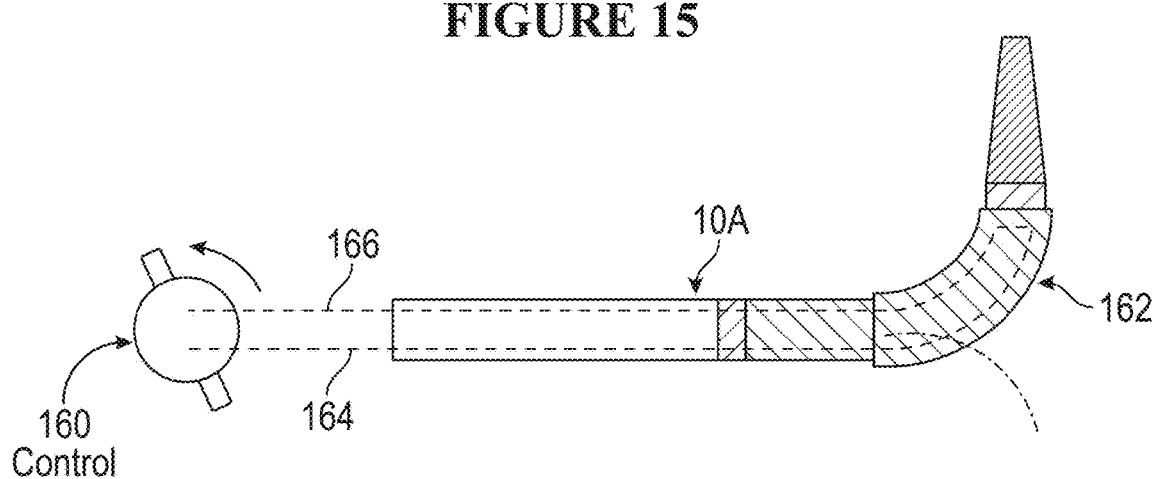

INTRAVASCULAR CATHETER WITH FLUOROSCOPICALLY VISIBLE INDICIUM OF ROTATIONAL ORIENTATION

CROSS-REFERENCE TO RELATED APPLICATIONS

This application claims priority to U.S. Provisional Patent Application No. 62/830,199, filed Apr. 5, 2019, and U.S. Provisional Patent Application No. 62/907,299, filed Sep. 27, 2019, the entire contents of both of which are incorporated herein by reference in their entireties.

BACKGROUND OF THE INVENTION

An interventional guide wire or other interventional device is often used in medical procedures that attempt to establish a pathway through a heavily stenosed or chronically occluded vessel. A chronically occluded vessel is referred to as containing a chronic total occlusion or CTO. During these procedures, the guide wire or device can only be of clinical benefit to establish vessel patency if it is advanced distally into the vessel true lumen.

One technique for restoring patency across a CTO involves advancing a guide wire through the intimal layer of the vessel wall and into the subintimal plane or space, where it can be further advanced distally beyond the CTO. Once in this sub-intimal plane beyond the CTO, it becomes difficult to navigate the guide wire or device back through the subintimal tissue layer to re-gain access into the vessel true lumen, sometimes referred to as a "reentry" into the vessel lumen from the sub-intimal space distally of the CTO. The layer of tissue that separates the vessel true lumen from the subintimal plane is typically in the range from 100 to 500 micrometers thick for vessels in the diameter range from 2 mm to 4 mm, and from 100 to 3000 microns thick, in the largest vessels of the body.

A variety of catheters have been proposed for reentry around a CTO. One is described and shown in U.S. Pat. No. 6,231,546. In this system, the re-entry catheter requires the operator to rotate a catheter shaft while observing a radiopaque marker on the catheter shaft to ensure that a side or lateral port is aimed at the true lumen of the blood vessel. Once the marker indicates the correct orientation of the lateral port, a cannula is extended through the lateral port in order to penetrate through the intimal layer of the blood vessel. It is believed that one drawback of this system is the requirement to rotate the catheter to the correct position while under fluoroscopic imaging otherwise an incorrect orientation of the cannula could cause failure to reenter the parent lumen and potentially cause damage to the vessel.

Another system is described and illustrated in US Patent Application Publication 2013/0072957. In this publication, a balloon is used to orient the cannula into the proper orientation for re-entry into the true vessel lumen. To achieve this, the catheter utilizes an asymmetrical catheter lumen for the cannula. It is believed that this system also suffers from a similar drawback in that the lateral port of the cannula must be oriented in the correct direction towards the true lumen while under fluoroscopy. This is to ensure that the cannula does not penetrate away from the true lumen, which could lead to internal hemorrhaging.

Despite the foregoing and other efforts in the prior art, there remains a need for an improved reentry catheter and method for traversing total chronic occlusions.

SUMMARY OF THE INVENTION

Disclosed is a reentry catheter for crossing a vascular occlusion. The catheter includes an elongate flexible tubular body, having a proximal end, a distal end and at least one lumen extending there through. A reentry zone on the tubular body includes at least two and preferably at least three or five or more exit apertures in communication with the lumen, the apertures rotationally offset from each other by at least about 15 degrees and aligned in a spiral pattern around the tubular body. In one implementation, three pairs of opposing apertures are provided.

A method of crossing a chronic total occlusion includes the steps of advancing a guidewire from a vascular lumen through the intima, into a subintimal space and distally beyond the occlusion. A reentry catheter is advanced over the guidewire and beyond the occlusion, such that at least one of a plurality of spirally aligned exit ports on the reentry catheter is rotationally aligned with the lumen. The guidewire is advanced through the at least one exit port to cross the intima and reenter the lumen. The reentry catheter may be removed, and a balloon catheter may be advanced over the wire and the balloon expanded in the subintimal space to create a neolumen that permits perfusion across the occlusion. A stent may be expanded in the neolumen to maintain patency across the occlusion.

There is provided, in accordance with another aspect of the present invention, a re-entry catheter for crossing a vascular occlusion. The catheter comprises an elongate flexible tubular body, having a proximal end, a distal end and at least one lumen extending there through. A reentry zone is defined on the tubular body, comprising at least two exit apertures in communication with the lumen, the apertures rotationally offset from each other by at least about 5 degrees, and the reentry zone is positioned within about 20 cm of the distal end of the tubular body.

The re-entry zone may be comprised of at least three apertures, or at least five apertures, arranged in a spiral configuration around the tubular body. At least one aperture may have a noncircular configuration and at least one aperture may have a major axis in parallel to a longitudinal axis of the tubular body, and a minor, transverse axis. At least one aperture has a minor axis diameter of at least about 0.025 mm.

In accordance with another aspect of the present invention, there is provided a method of crossing a chronic total occlusion. The method comprises the steps of advancing a guidewire from a vascular lumen through the intima, into a subintimal space and distally beyond the occlusion. A reentry catheter is advanced over the guidewire and beyond the occlusion, such that at least one of a plurality of exit ports on the reentry catheter is rotationally aligned with the lumen. The guidewire is advanced through the at least one exit port to cross the intima and reenter the lumen.

The method may additionally comprise the step of applying vacuum to the central lumen or secondary lumen to draw adjacent tissue against one or more side ports. Vacuum may also be used to aspirate hematoma or other embolic material into one or more side ports, and/or the distal guidewire opening into the central lumen.

The method may further comprise the step of proximally retracting the catheter, leaving the guidewire extending into the lumen distally of the occlusion. A balloon catheter may be advanced over the wire and the balloon expanded in the subintimal space. A stent may be expanded in the subintimal space to maintain patency of a neolumen that permits perfusion across the occlusion.

In accordance with a further aspect of the present invention, there is provided a reentry catheter for crossing a vascular occlusion, comprising an elongate flexible tubular body, having a proximal end, a distal end and at least one lumen extending therethrough; and a reentry zone on the tubular body, comprising at least three opposing pairs of side wall exit apertures in communication with the lumen, each opposing pair of apertures rotationally offset from an adjacent opposing pair of apertures.

The reentry catheter may additionally comprise a reinforcing ring surrounding each aperture. The catheter may be provided with six reinforcing rings, one for each aperture, and the reinforcing rings may be connected together by a frame in the side wall which may be in the form of a tubular support. The reinforcing rings may comprise a radiopaque material. The frame may comprise a helical strut extending between a first and second axially spaced apart opposing pairs of side wall exit apertures.

The catheter may further comprise an inflatable balloon on the tubular body, in communication with a second, inflation lumen extending axially through the tubular body. A guidewire lumen may extend axially through the tubular body between a proximal port and a distal port, and the proximal port may be spaced distally apart from the proximal end or at the proximal end of the tubular body. The proximal port is within about 20 cm of the distal end of the tubular body.

There is also provided an intravascular catheter with fluoroscopically visible indicium of rotational orientation. The catheter comprises an elongate flexible tubular body, having a proximal end, a distal end and a tubular side wall defining at least one lumen extending there through; and first and second opposing pairs of radiopaque rings in the side wall, spaced axially apart from each other; wherein a first transverse axis extending through the first pair of rings is rotationally offset from a second transverse axis extending through the second pair of rings.

The intravascular catheter may further comprise an aperture in the side wall through each ring. The catheter may further comprise a frame connecting the rings, which may comprise one or more struts configured to provide a flexible hinge. At least a portion of the frame in between the first and second opposing pairs of rings in one implementation comprises a spring hinge in the form of at least one helical strut.

In accordance with a further aspect of the present invention, there is provided a subassembly for integration into the wall of a catheter. The subassembly comprises a tubular body having a plurality of aperture portions and intervening hinge portions. Each aperture portion includes a first and a second aperture carried on opposing sides of the tubular body. A first axis extending transversely through the tubular body and the first and second apertures of a first aperture portion is rotationally offset from a second axis extending transversely through the tubular body and the first and second apertures of a second aperture portion.

The hinge portion may comprise a helical strut. The aperture portions and intervening hinge portions may be parts of a unitary body which may be laser cut from a tube. Each aperture may be formed within an eyelet separated from an adjacent eyelet by a hinge portion.

An aperture may have a minor axis and a transverse major axis having a length of at least about 150% of the length of the minor axis. The subassembly body may have a wall thickness of no more than about 0.05 inches, and in some implementations no more than about 0.004 inches.

The subassembly may have at least three pairs of opposing apertures with intervening hinge portions between each aperture pair. A first hinge portion may comprise a helical strut having a first pitch and a second hinge portion spaced apart from the first hinge portion by an aperture pair portion, may have a helical strut having a second, different pitch.

Further features and advantages of the invention will become apparent to those of skill in the art from the following description taken together with the associated drawings and claims.

BRIEF DESCRIPTION OF THE DRAWINGS

FIGS. 5A and 5B show geometric aspects of the exit ports.

FIG. 14 illustrates different fluoroscopic visualization options.

FIG. 15 is a schematic illustration of a reentry catheter distal end having an active deflection mechanism.

DETAILED DESCRIPTION OF THE PREFERRED EMBODIMENT

Figure 1:
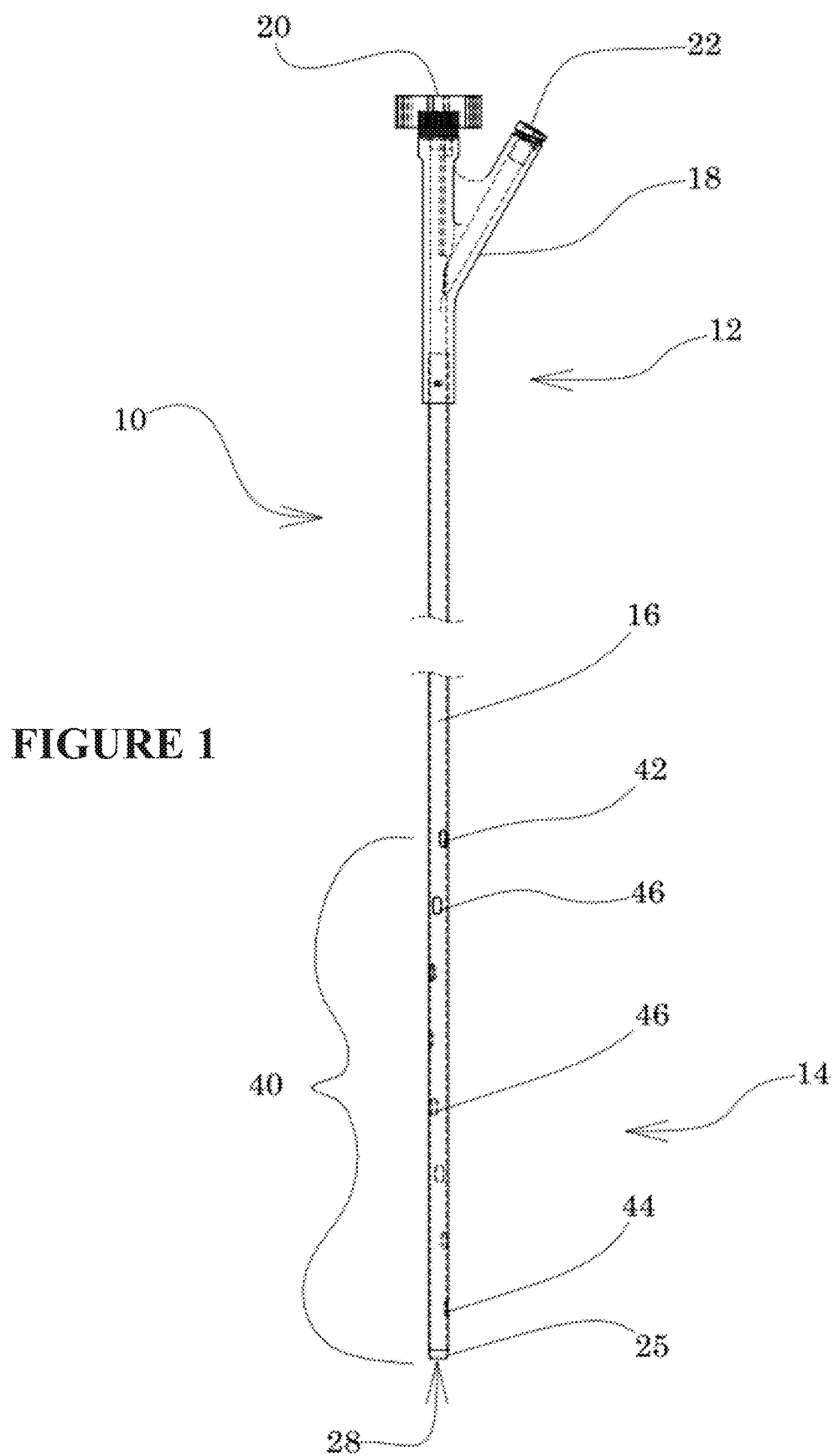
FIG. 1 is a side elevational view of a reentry catheter in accordance with the present invention.

Referring to FIG. 1, there is disclosed a catheter 10 in accordance with one aspect of the present invention. Although primarily described in the context of a reentry catheter with a single central lumen, catheters of the present invention can readily be modified to incorporate additional structures, such as permanent or removable column strength enhancing mandrels, two or more lumen such as to permit drug or irrigant infusion or to supply inflation media to an inflatable balloon, or combinations of these features, as will be readily apparent to one of skill in the art in view of the disclosure herein.

The catheters disclosed herein may readily be adapted for use throughout the body wherever it may be desirable to create an extravascular access or a neolumen, such as to traverse a CTO or otherwise exit and reenter the lumen. For example, catheter shafts in accordance with the present invention may be dimensioned for use throughout the coronary and peripheral vasculature, the gastrointestinal tract, the urethra, ureters, Fallopian tubes and other lumens and potential lumens, as well.

The catheter 10 generally comprises an elongate tubular body 16 extending between a proximal end 12 and a distal functional end 14. The length of the tubular body 16 depends upon the desired application. For example, lengths in the area of from about 120 cm to about 160 cm or more are typical for use in femoral access percutaneous transluminal coronary applications. Intracranial or other applications may call for a different catheter shaft length depending upon the vascular access site, as will be understood in the art.

The proximal end 12 of catheter 10 is additionally provided with a manifold 18 having one or more access ports as is known in the art. Generally, manifold 18 is provided with a guidewire port 20 in an over-the-wire construction, and an optional side port 22 depending upon the desired functionality. Additional access ports may be provided as needed, depending upon the functional capabilities of the catheter. Manifold 18 may be injection molded from any of a variety of medical grade plastics, or formed in accordance with other techniques known in the art.

The tubular body 16 is provided with a reentry zone 40, extending between a proximal exit port 42 and a distal exit port 44, configured to permit exit of a guidewire therethrough. Preferably at least three or five or seven or more exit ports or port pairs are provided, arranged circumferentially offset from each other so that regardless of the rotational orientation of the catheter in the vessel, at least one exit port will be facing the direction of the true vessel lumen. The exit ports may be arranged in a spiral, with axially adjacent ports rotated from each other about the longitudinal axis of the catheter within the range of from about 5 degrees and 90 degrees, preferably between about 10 degrees and 60 degrees, and in some embodiments between about 15 degrees and 35 degrees.

In an axial direction, adjacent ports may be spaced apart by a distance within the range of from about 2 mm to about 4 mm or about 5 mm and about 15 mm. Side ports define a reentry zone 40 having an axial length from the proximalmost port 42 to the distalmost port 44 of at least about 2 mm and generally less than about 20 mm; in many implementations between about 4 mm and 15 mm. The side ports define a spiral that extends at least about 45 or 90 degrees around the catheter side wall but typically no more than about 360 degrees and in certain embodiments within the range of from about 270 degrees and 450 degrees.

Figure 2:
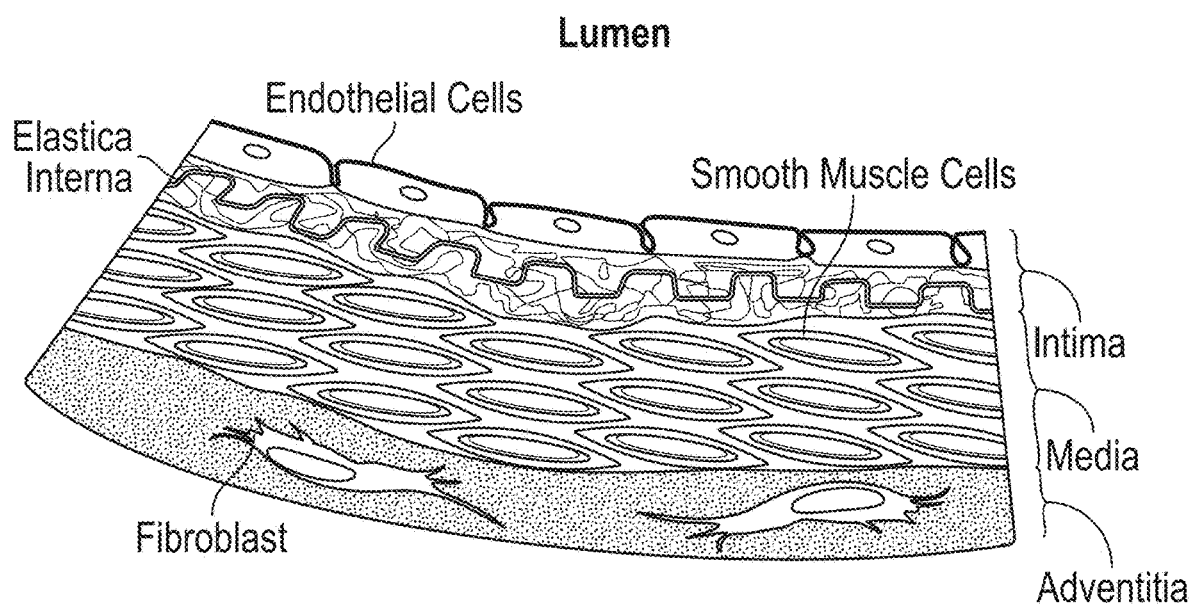
FIG. 2 shows the anatomy of a coronary artery.

Referring to FIG. 2 the coronary artery walls are made up of three main layers. The intima is the innermost layer consisting of a single layer of endothelial cells. The fibromuscualar media includes nonstriated myocytes. The adventitia is the outermost layer composed of collagen and elastin.

The intima layer can thicken considerably over time, occluding the blood flow through the artery. A chronic total occlusion (CTO) is a complete blockage of the artery. The present invention relates to a method to treat a CTO by creating a new lumen in the subintimal space (between the adventitia and intima) in order to allow blood flow in the artery around the occlusion.

Figure 3A:
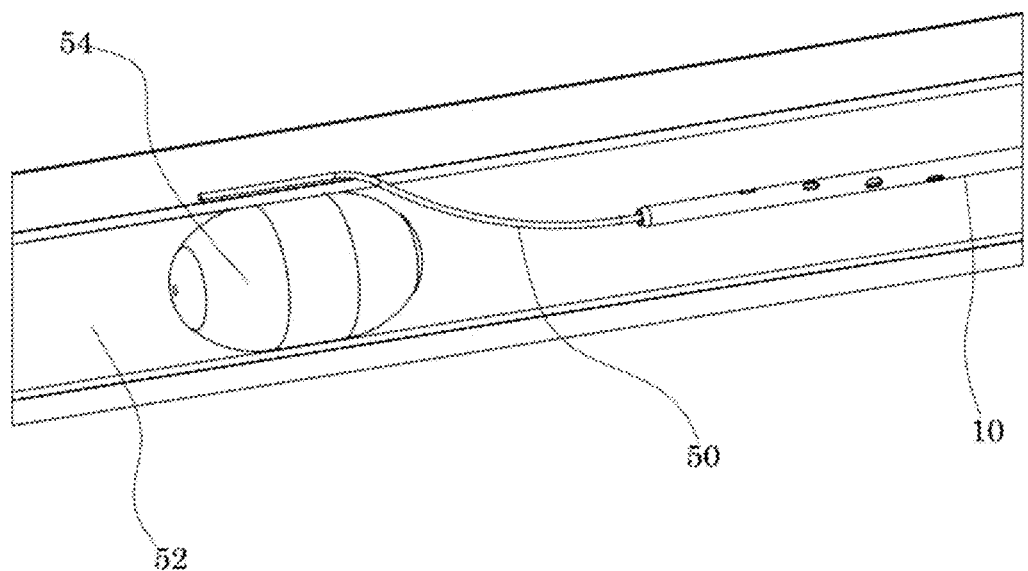
FIG. 3A shows a guidewire entering a subintimal space to cross an occlusion.
Figure 3B:
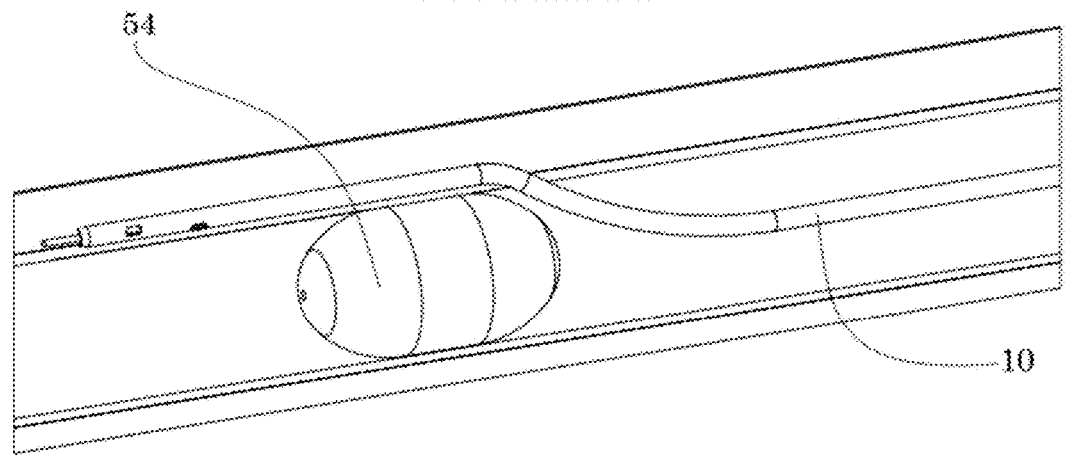
FIG. 3B shows a reentry catheter tracking over the guidewire and through the subintimal space.

Referring to FIG. 3A, a guidewire 50 is advanced through the arterial lumen 52 to the proximal side of an obstruction to be treated, such as a CTO 54. Progress of the wire 50 may be impeded or deflected due to the CTO. If the guidewire cannot cross the lesion, the guidewire may be passed distally beyond the lesion by way of an intentional dissection, and is advanced in a created subintimal channel between the intimal and medial layers of the arterial wall. This allows the guidewire 50 to cross the CTO 54 via the subintimal space. A reentry catheter 10 is then advanced over the guide wire 50, following the guidewire from the native arterial lumen, through the dissection and into the subintimal space. See FIG. 3B. The guidewire 50 may thereafter be retracted into the guide catheter.

Figure 3C:
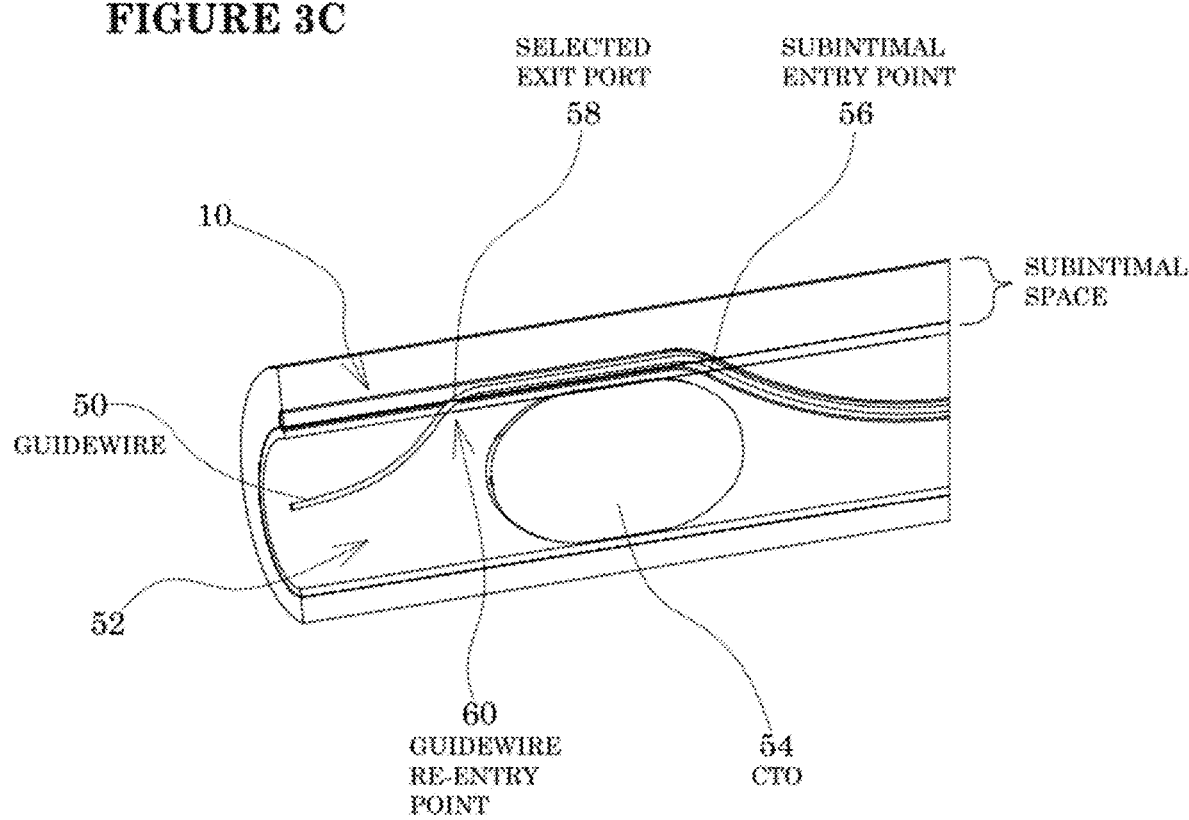
FIG. 3C shows the guidewire passing out of a selected exit port and back through the intima and into the true lumen distal to the occlusion.

As seen in more detail in FIG. 3C, the reentry catheter 10 exits the native lumen at a subintimal entry point 56, and travels distally within the subintimal space. The guide wire 50 may thereafter be advanced distally within the reentry catheter 10 and rotated to find the exit port having the desired axial and rotational orientation to direct the guidewire 50 towards the native vascular lumen 52. The guidewire may thereafter be distally advanced to exit through the selected exit port 58, distal of the lesion 54, for reentry into the native vascular lumen 52 at guidewire reentry point 60.

Figure 3D:
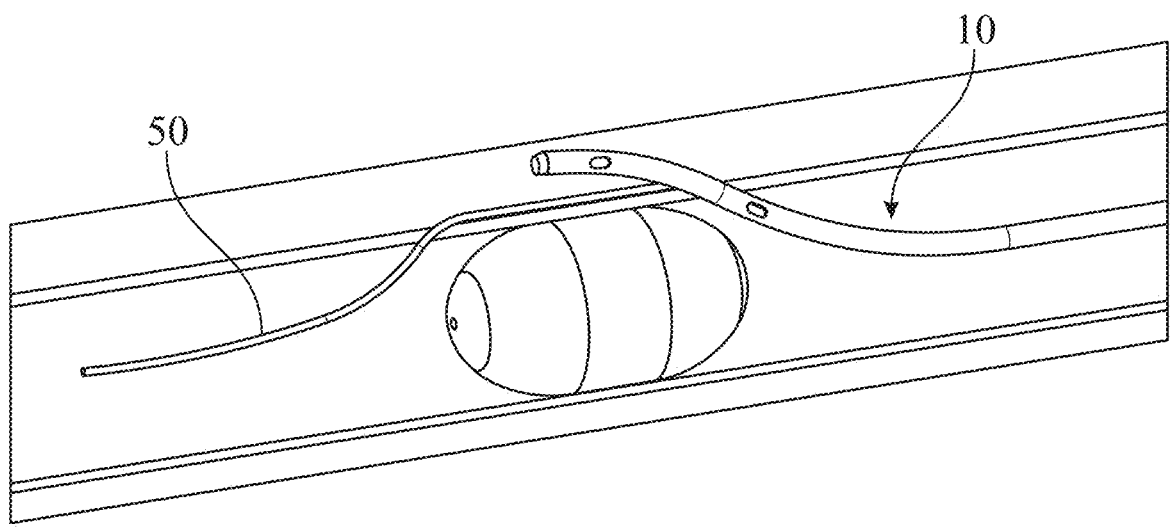
FIG. 3D shows proximal retraction of the reentry catheter while leaving the guidewire in position across the occlusion.

Once the guidewire 50 has correctly reentered the lumen distally of the CTO, the reentry catheter 10 can be proximally retracted from the subintimal space leaving the guidewire in position via the neo lumen across the CTO. See FIG. 3D. The reentry catheter can thereafter be withdrawn from the artery.

Figure 3E:
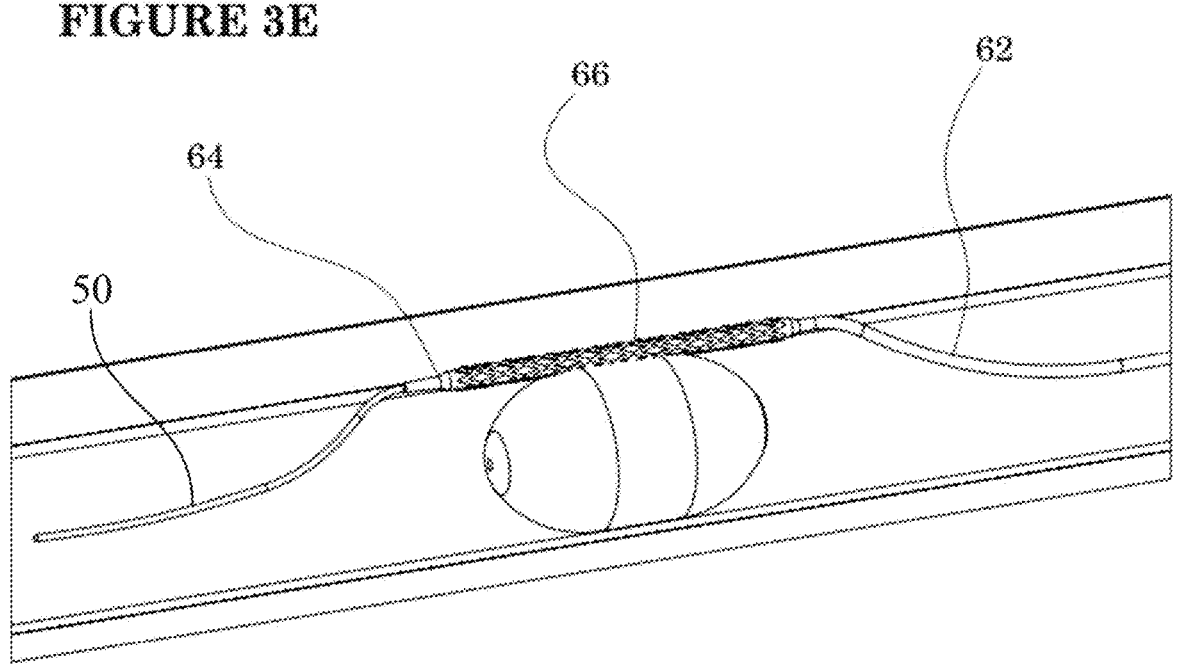
FIG. 3E shows a balloon catheter carrying a balloon expandable stent positioned across the occlusion via the subintimal space.
Figure 3F:
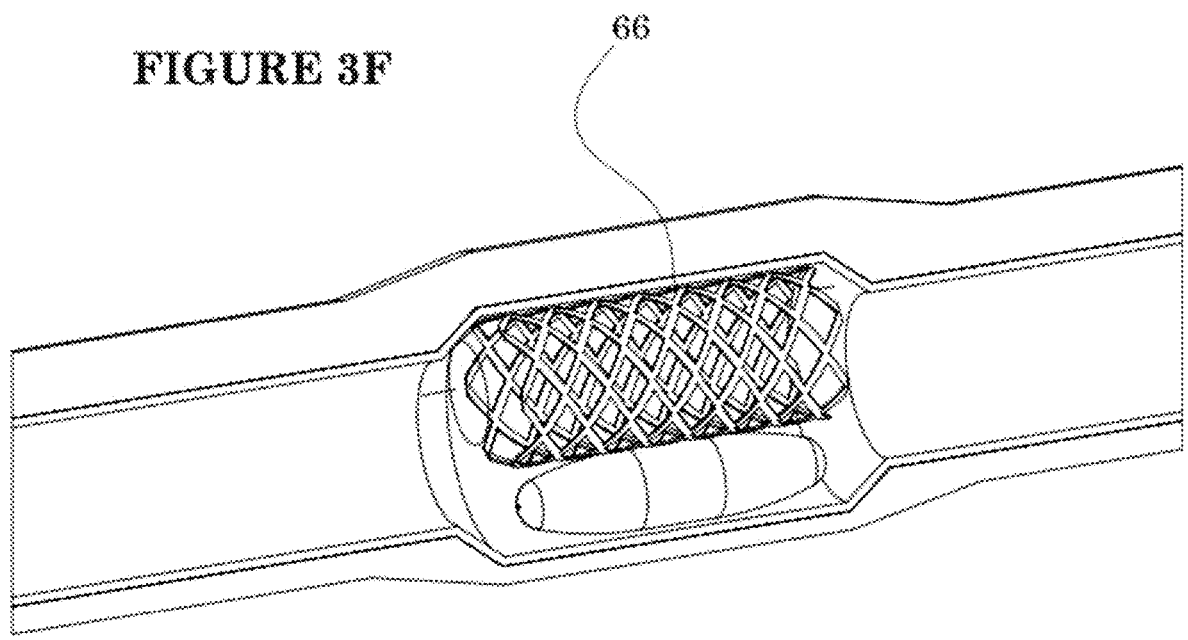
FIG. 3F shows the catheter removed, leaving the stent expanded to support a neolumen to permit perfusion across the occlusion in the native lumen.

Any of a variety of procedures can be accomplished with the guidewire in position across the CTO. For example, referring to FIG. 3E, a balloon catheter 62 can be advanced over the guide wire 50 to position an inflatable balloon 64 in the subintimal space. Dilitation of the balloon can open a flow channel to cross the CTO via the subintimal space. The balloon may carry a balloon expandable stent 66 which can be expanded spanning the CTO to support the neolumen against collapse following removal of the balloon as is understood in the art. Alternatively a self-expanding stent may be deployed across the CTO, preferably following a mechanical dilatation (e.g., balloon dilatation step).

Additional details of the catheter design may be seen with reference to FIGS. 4A-5A. A plurality of successive axially spaced exit ports 46 are arranged in a spiral such as a helix about the longitudinal axis of the catheter. The guide wire 50 may have a pre-bent tip so that it is biased laterally against the inside diameter of the reentry catheter sidewall. The guide wire may be distally advanced and rotated to align, for example, with distalmost exit port 44 and advanced through that port. See FIG. 4A.

Figure 4A:
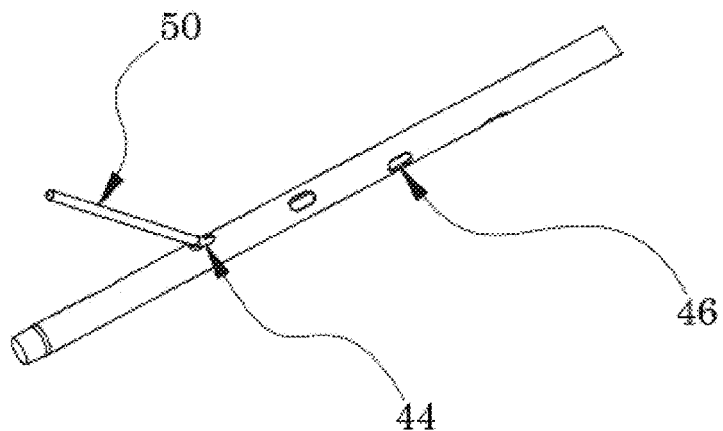
FIG. 4A shows a reentry catheter with a guidewire exiting a first exit port at a first rotational orientation.
Figure 4B:
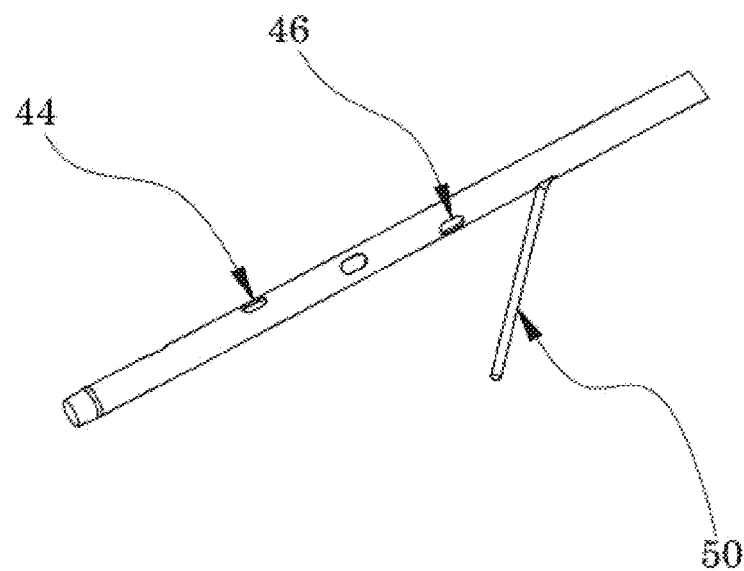
FIG. 4B shows a reentry catheter with a guidewire exiting a second exit port at a second rotational orientation.

Alternatively, if the native arterial lumen is in a different orientation relative to the reentry catheter 10, the guide wire can be axially repositioned and rotated to align and exit via a second different exit port to reenter the arterial lumen at a different orientation as seen in FIG. 4B.

Referring to FIGS. 1 and 5A, the proximalmost port 42 and distalmost port 44 define reentry zone 40 along which a plurality of ports 46 will generally encompass at least about 270 and preferably about 360 degrees around the circumference of the reentry catheter 10. Generally between about 4 and 16 ports are provided with one embodiment between about six and ten ports. A reentry zone 40 having eight ports aligned along a 360 degree spiral results in 45 degrees of rotation between adjacent ports. Preferably, ports are arranged in sets of opposing pairs, as is discussed further below.

Referring to FIG. 5B, the ports will generally have a major axis 80 extending longitudinally along the catheter and a minor, transverse axis 82 extending circumferentially around the tubular body. The major axis 80 will typically be within about 15 degrees or 10 degrees or less from parallel with the catheter longitudinal axis and may be about parallel to the longitudinal axis as shown in FIG. 5B, or aligned with the spiral on which the ports reside.

The major axis 80 is generally longer than the minor axis 82, and may be at least about 150%, or 175% or 200% or more than the length of the minor axis 82. In some implementations of a reentry catheter, the minor axis 82 is within the range of from about 0.012 inches to about 0.20 inches; or about 0.014 inches to about 0.018 inches. The major axis 80 is within the range of from about 0.024 inches to about 0.046 inches, or about 0.030 inches to about 0.042 inches. In one example, the port is about 0.016 by about 0.034 inches in a catheter having an OD of about 0.038 inches. The minor axis of the port may be less than about half of the tubular body OD and over about half of the catheter body ID.

Preferably, the ID of the tubular catheter body is at least about 120% or 150% or 175% or 200% or more of the OD of the GW intended to be used with the catheter. In one implementation, a catheter having an ID of about 0.028 inches is intended for use with a 0.014 inch guide wire. The difference between the diameter of the guide wire and the ID of the catheter is generally at least about 0.005 or about 0.010 or more, to facilitate manipulation of the guidewire and directing the guidewire towards a desired exit port.

In addition, the relatively large space between the guidewire and the ID of the catheter facilitates application of vacuum (e.g., up to about 29 mm Hg, or 20 mm Hg) while the guide wire is in position extending through the tubular body, which allows negative pressure applied to the central lumen to produce suction at the exit ports for anchoring the catheter to the adjacent tissue. Anchoring the reentry zone to adjacent tissue may be desirable to stabilize the catheter and facilitate penetration during the step of puncturing tissue with the guidewire to reenter the vessel lumen distally of the obstruction.

The exit ports 46 may be spaced apart axially by a distance within the range of from about 0.05 inches to about 0.25 inches or in some embodiments from about 0.08 inches to about 0.20 inches. Multi-sized ports can be provided, with a first set of guidewire exit ports and a second set of smaller aspiration ports arrayed among the guidewire ports. Multiple sizes of ports may also be utilized for infusion of therapeutic agents.

Figure 6A:
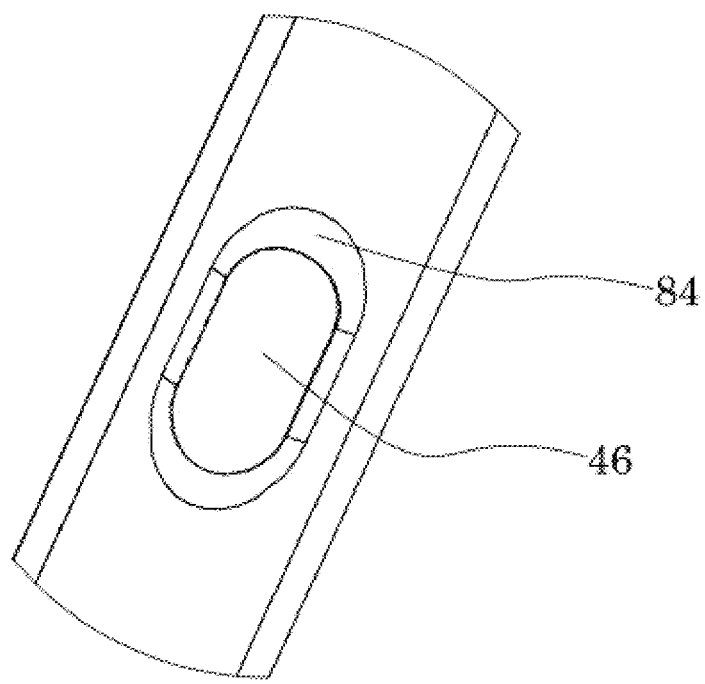
FIGS. 6A-6C show various exit port details.
Figure 6B:
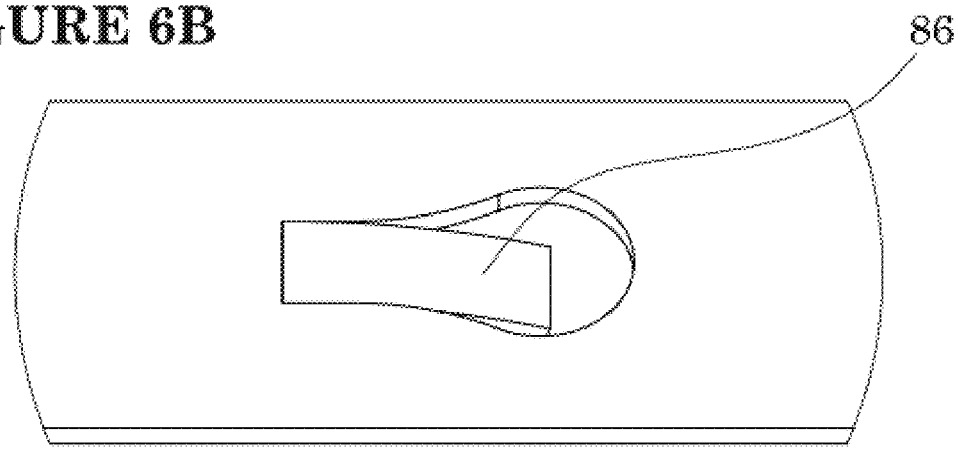
Figure 6C:
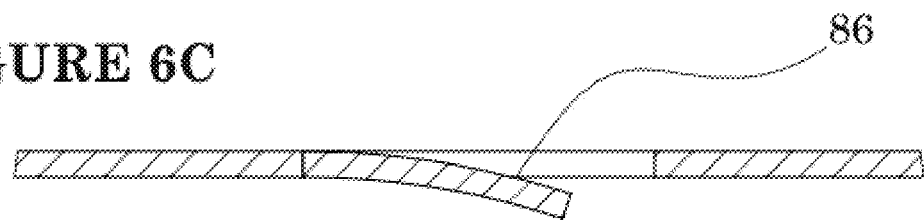
Figure 7A:
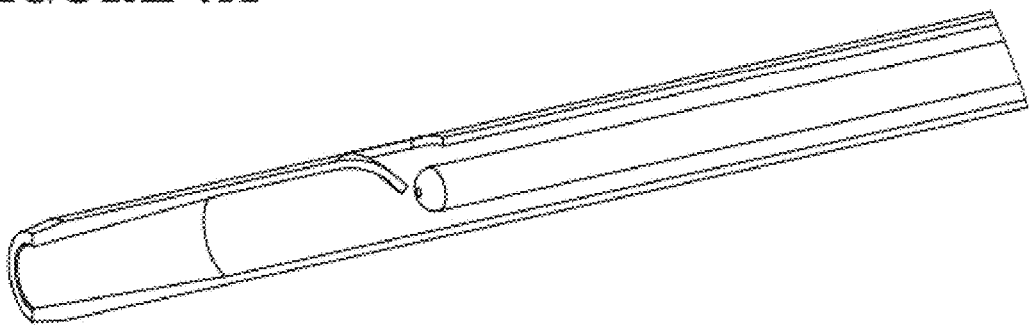
FIGS. 7A-7B show lateral exit of a guide wire through an exit port with an exit ramp.
Figure 7B:
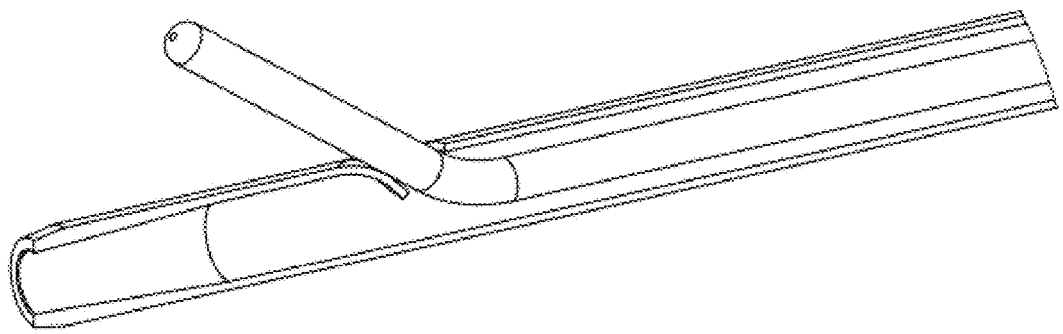

A variety of port geometries and ramp geometries may be utilized to optimize control over port selection and guidewire exit. Referring to FIG. 6A, the edge of the catheter wall at the distal end of a port 46 may be provided with a ramped surface 84 configured to facilitate exit of the guidewire. Alternatively, a ramp surface 84 may be provided by forming a tab 86 that inclines radially inwardly in a proximal direction into the lumen. A guidewire with a laterally biased tip can be rotated and advanced until the tip enters the port assisted by the ramp 84 on the sidewall or on a tab. See FIGS. 7A and 7B.

Figure 8:
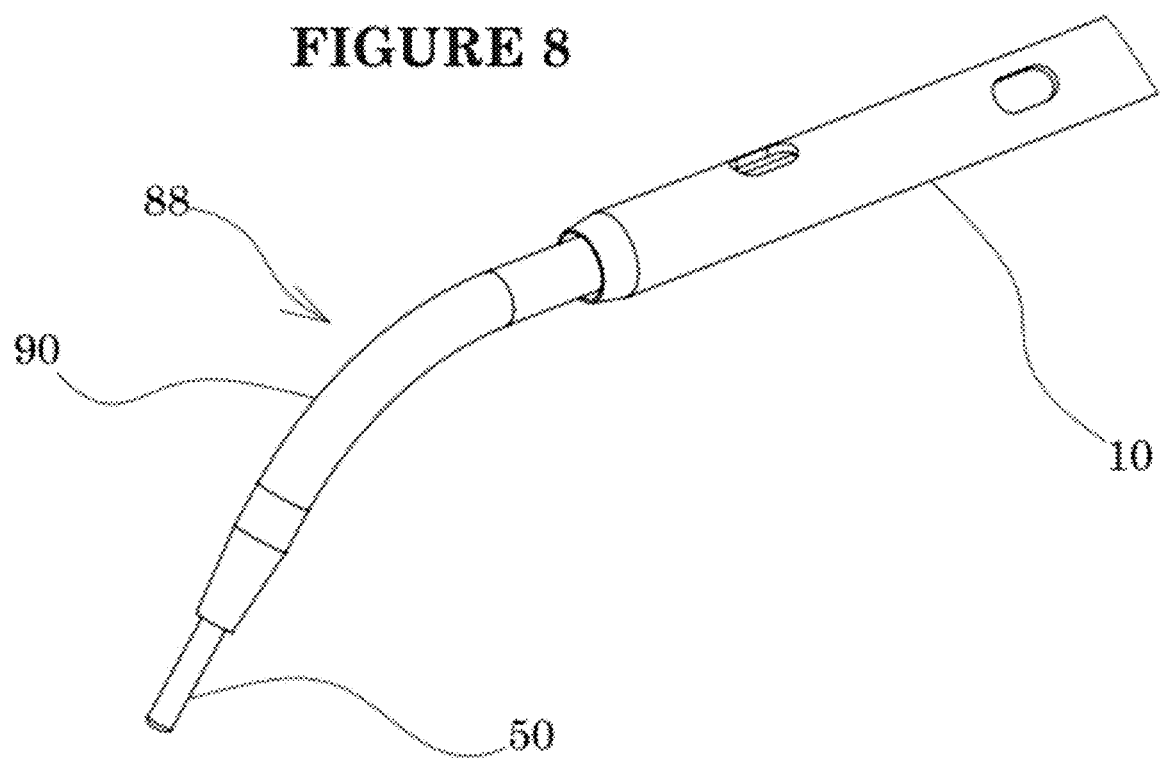
FIG. 8 shows a biased deflection guide for directing a guidewire toward the native lumen.

Deflection of the guidewire may also be facilitated by an intermediate deflection element such a deflection guide 88. See FIG. 8. The deflection guide 88 may comprise a shape memory (e.g., Nitinol) tube 90 that is preset to an angle upon proximal retraction of or distal advance from of a restraint.

Figure 9:
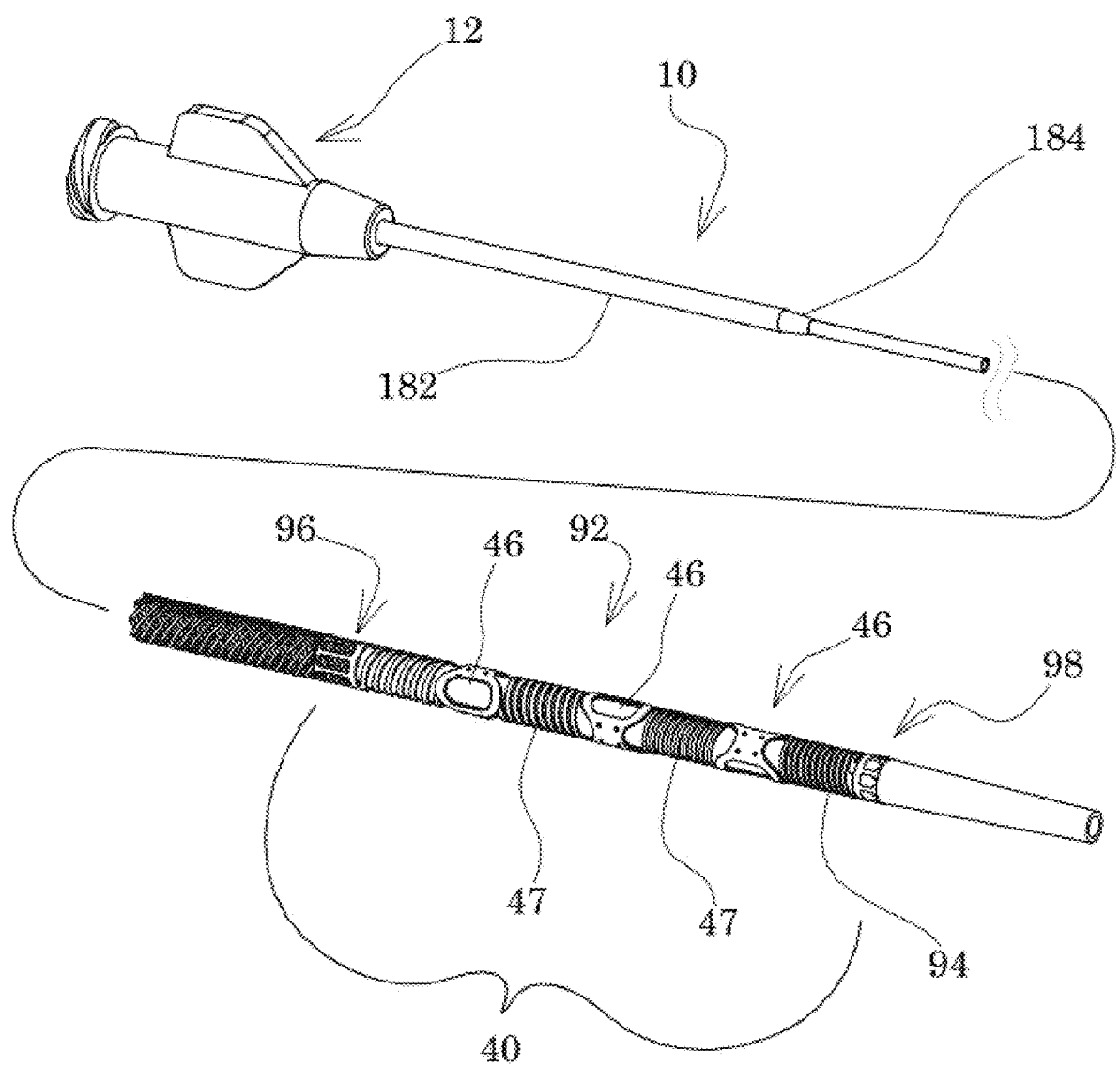
FIG. 9 shows a reentry catheter with a reinforced reentry zone.

Referring to FIG. 9, there is illustrated a reentry catheter 10 including a reentry zone support 92 extending throughout the reentry zone 40. The support 92 includes a tubular body 94 extending between a proximal end 96 and a distal end 98 and which carries a plurality of exit ports 46 spaced apart by a plurality of intervening flexible links 47. Additional detail is described in connection with FIGS. 10A-10E.

Extending proximally from the support 92, which may be a metallic insert, is a kink resistance and torque transmission feature such as a braided tubular sidewall component 186. Braid 186 may be a stainless steel braid having between about 12 and 20 filaments, and in one implementation 16 rectangular filaments having a width that is at least about 3× or 4× the thickness. The braid may overlay a coil layer 188, which in one implementation is a four filar coil of 0.001" tungsten wire at about 0.008" pitch. The braid 186 overlaps the proximal end of the support 92, but in the illustrated implementation the distal end of the coil 188 is spaced proximally apart from the proximal end of the support 92.

FIG. 10 shows first, second and third aperture pairs 130, 132 and 134. At least a first eyelet frame 100 comprising an annular strut 102 encircles a guidewire exit port or aperture 104A on a first side of the tubular body 94. In the illustrated embodiment, the first eyelet frame 100 is spaced apart from the proximal end 96 by a first flexible link 106 in the form of an elongated helical strut 108. Proximal end 96 is additionally provided with a plurality of anchors such as at least about four or six or eight or more proximally extending ribs 110, for facilitating attachment to the outer surface of an underlying catheter body component such as a woven or braided reinforcement layer as shown in FIG. 10C.

A second eyelet frame 112 in the form of a second annular strut 114 defines a second aperture 116A. Second eyelet frame 112 is space distally apart from the first eyelet frame 100 by a second flexible link 118 in the form of a second helical strut 120. The total number of apertures in a reentry zone on a particular reentry catheter can be varied depending upon the desired clinical performance, as has been discussed elsewhere here in.

Figure 10A:
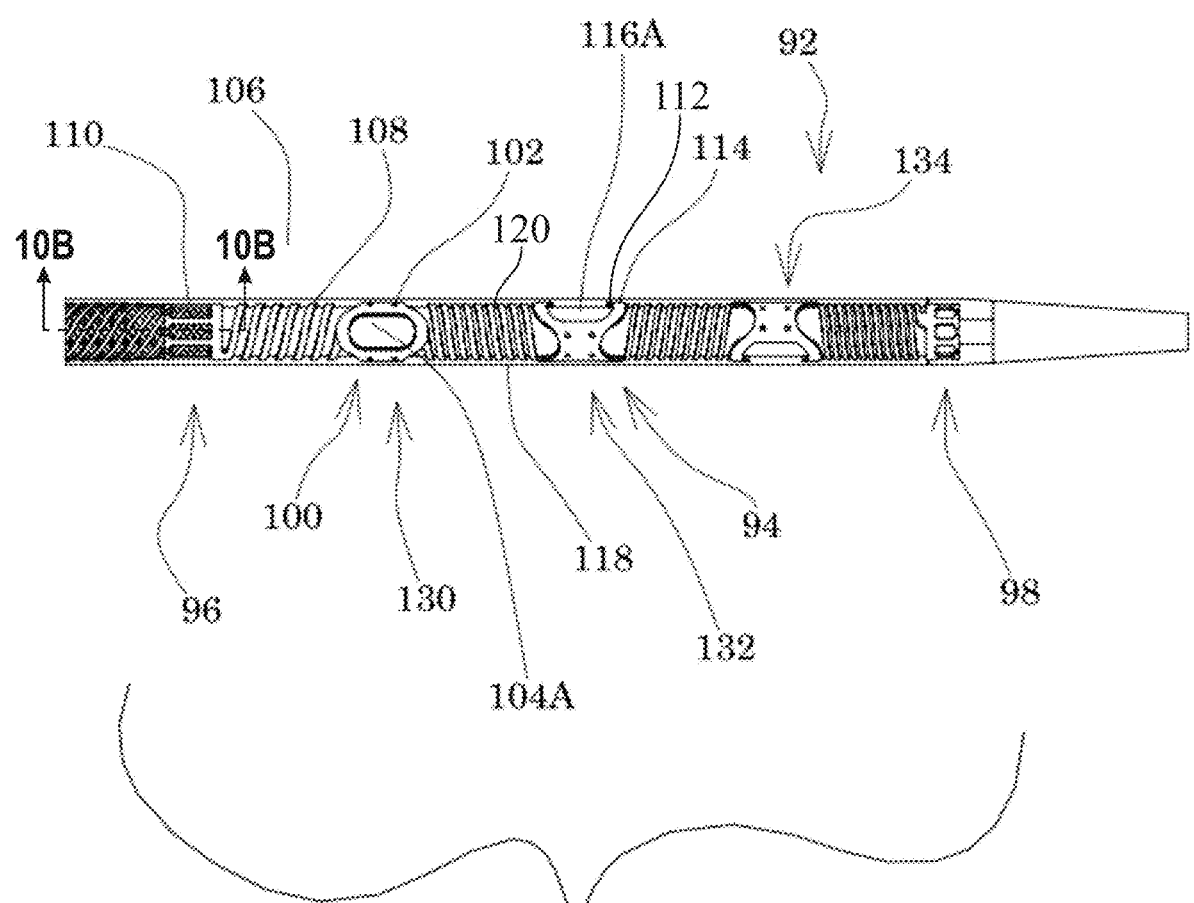
FIG. 10A is a side elevational view of a reinforcing insert for supporting the reentry zone.
Figure 10B:
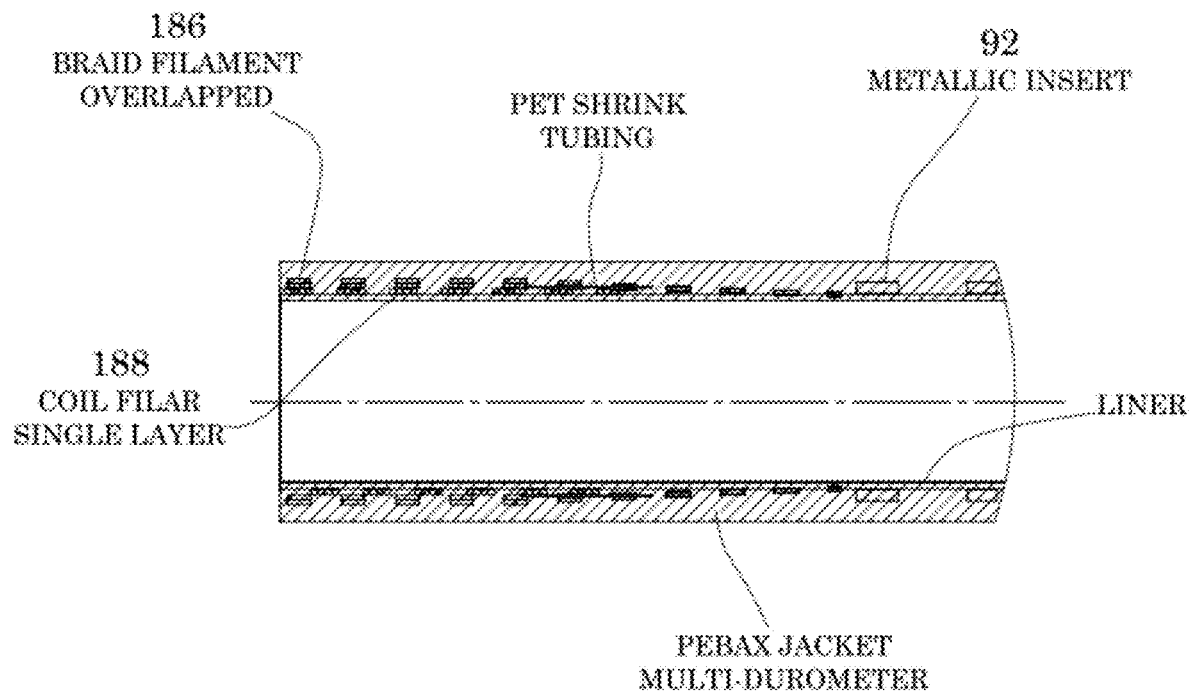
FIG. 10B is a side elevational cross section as taken along line 10B-10B of FIG. 10A through the catheter wall at the transition between the braid and the proximal end of the reentry zone support.
Figure 10C:
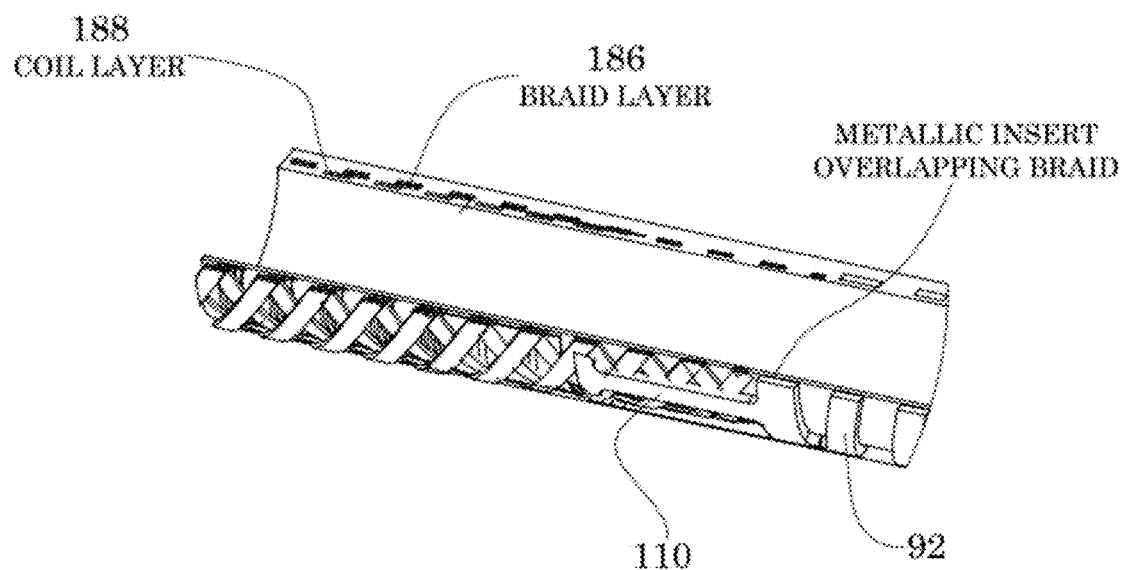
FIG. 10C is a perspective view of the cross section shown in FIG. 10B.
Figure 10D:
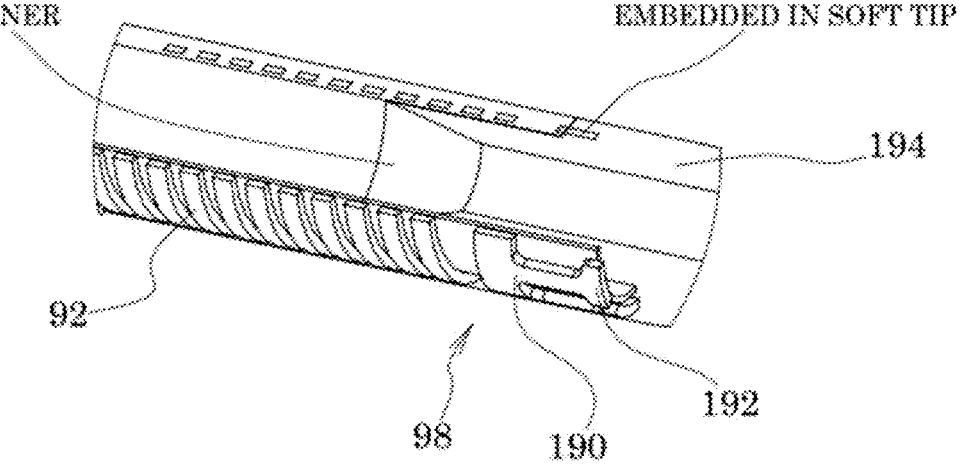
FIG. 10D is a perspective cross sectional view of the transition between the distal end of the reentry support and the catheter tip.
Figure 10E:
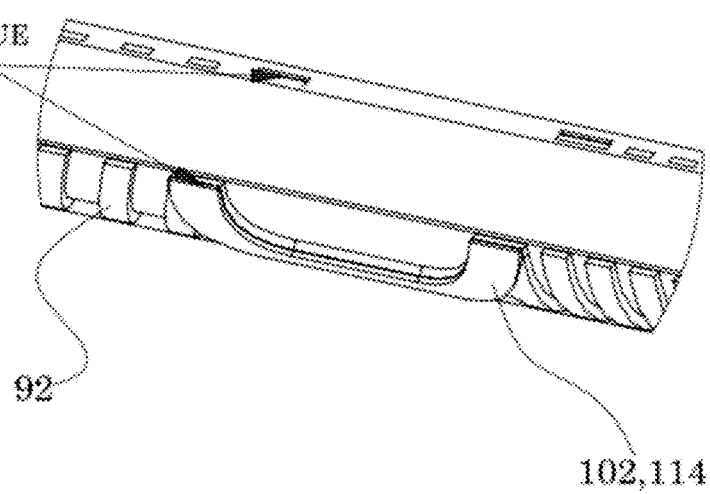
FIG. 10E is a perspective cross sectional view of an eyelet formed by the reentry support, having a radiopaque overlay surrounding the aperture.

Referring to FIG. 10D, the distal end of the reentry support 92 is provided with at least about four or six or eight or more tip anchors such as axially extending ribs 190. Ribs 190 may be provided with a circumferential segment 192 to create an interference fit when embedded in the polymer of the tip 194, which may comprise 35D PEBAX®, which is the trade name for polyether block amide. As shown in FIG. 10E, selected portions of the reentry support may be provided with a radiopaque marker such as a radiopaque coating layer. In the illustrated embodiment, the annular struts or eyelets that define the ports are provided with a layer of radiopaque material such as a Pt/Ir alloy, allowing an opposing port pair to appear as an oval aperture when aligned with the viewing axis.

Figure 11A:
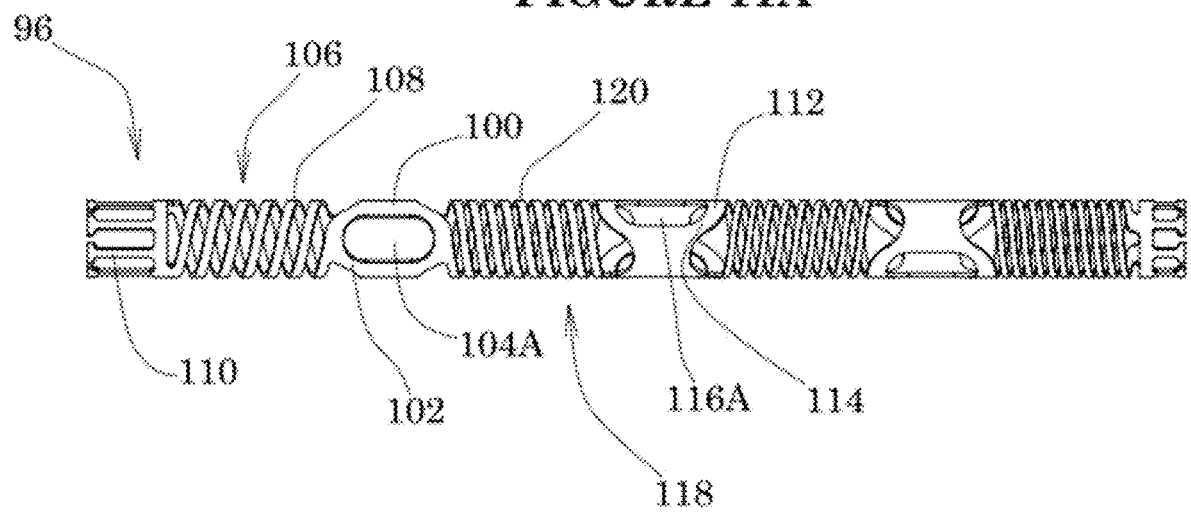
FIGS. 11A, 11B and 11C show three rotational orientations of a reentry zone support.
Figure 11B:
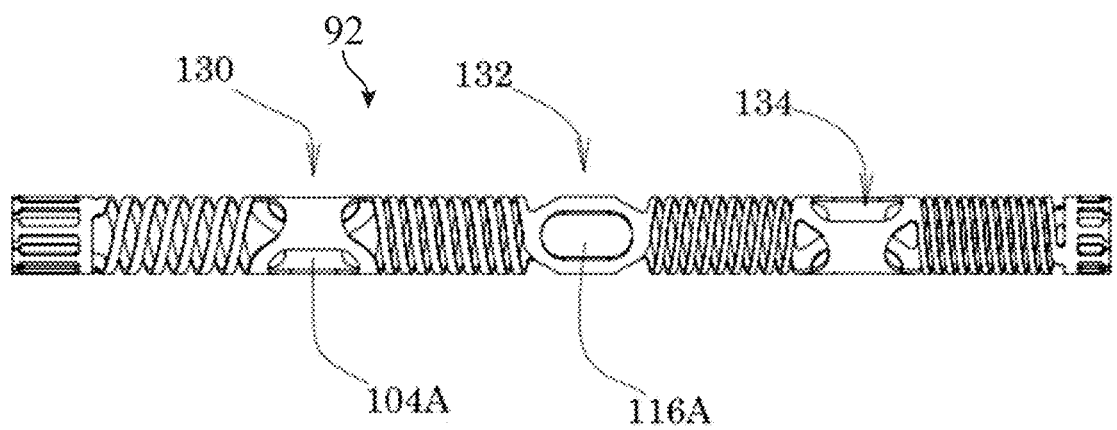
Figure 11C:
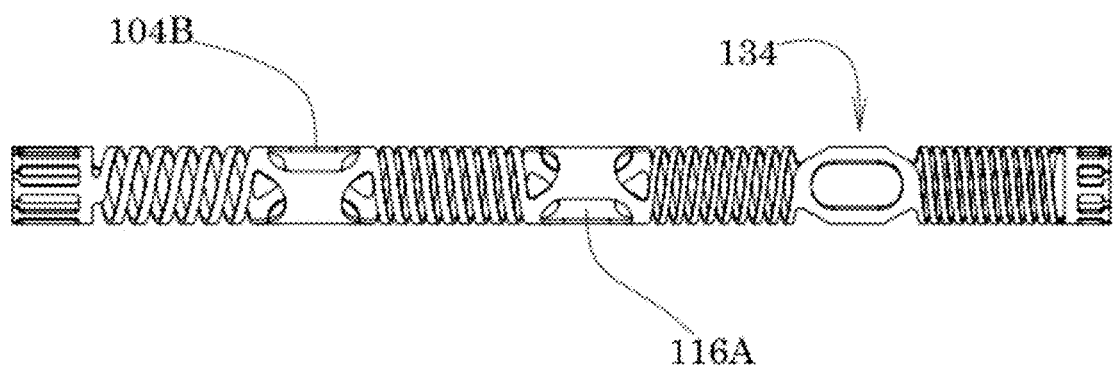

As seen in FIGS. 11A-C, a six port implementation is shown in which each aperture on a first side of the tubular body is paired with a second opposing aperture on the opposite side of the tubular body to form first, second and third aperture pairs 130, 132 and 134. A support 92 viewed from the perspective of FIG. 11A along an axis that extends at a perpendicular through each of the first and second windows 104A and 104B of the first aperture pair 130 appears under fluoroscopic visualization as a dark ring surrounding an opening, or an "O" or other indicium of a first rotational orientation.

The support 92 as shown in FIG. 11B has been rotated about its longitudinal axis by 60° compared to FIG. 11A. Viewed from the same viewing angle, the first aperture pair 130 is no longer aligned with the viewing axis so the window 104A has visually disappeared. Instead a sidewall of the tubular body becomes opaque such as in the form of an "X" or other indicium of a second rotational orientation. The first and third aperture pairs 130, 134 appear as an X or other indicia of non alignment. A further rotation of the support through an additional 60 degrees produces the view shown in FIG. 11C, in which the visualized "O" has moved to the third aperture pair 134.

Thus, the white "O" will progress along the length of the support from exit port pair to next adjacent exit port pair, as a function of rotational orientation. In this manner, the clinician can determine the rotational orientation of the distal end of the catheter under fluoroscopic visualization by tracking the location of the 0 and the X's relative to catheter rotation. This facilitates rotational alignment of the catheter relative to the true lumen, and selection of the appropriate exit port for launching the guidewire through the selected port and in the direction of the true lumen.

Figure 11D:
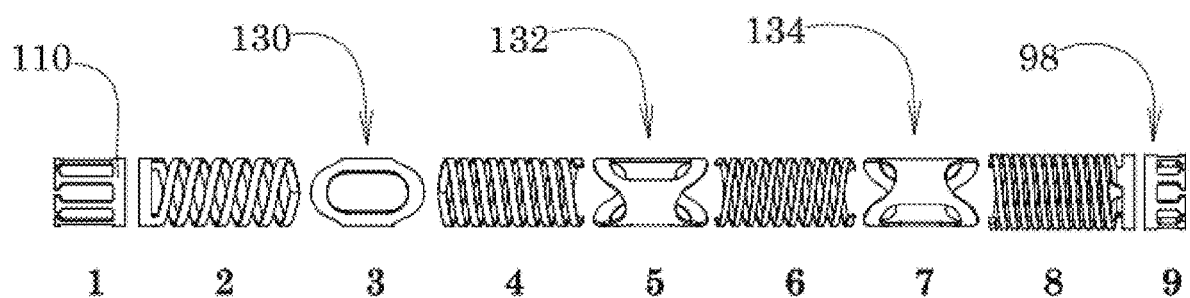
FIG. 11D is an exploded side elevational view of the reentry zone support of FIG. 11A.

Referring to FIG. 11D, there is illustrated an exploded view of the different functional components of the support. The components may be separately formed and connected such as by welding, or the entire assembly may be cut from a single piece of tubestock such as by laser cutting, EDM or other techniques known in the art.

Trackability and pushability are catheter characteristics that rely on the ability for the distal end of the catheter to push through the tortuous anatomy of the cardiac arteries. The consistency of the bending moments throughout the catheter shaft have significant impact on these use characteristics. The illustrated support insert comprises nine discrete regions, labelled 1-9 in FIG. 11D.

1. The proximal end is provided with a plurality of engagement structures such as at least two or four or six or more axially extending fingers designed to overlap and intertwine with the braid and coil reinforcement of the shaft.

Figure 11E:
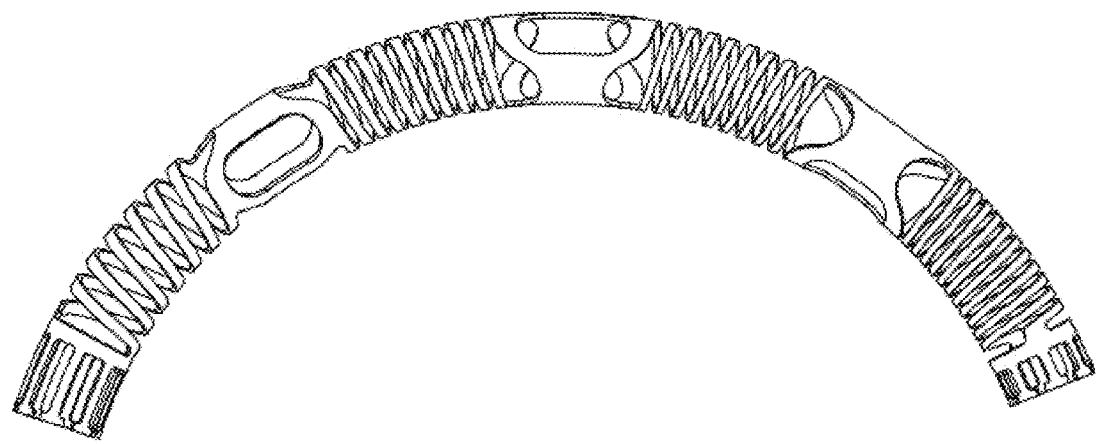
FIG. 11E is a side elevational view of the support of FIG. 11A, in a curved configuration.

2. First, proximal, single or dual start, first direction such as clockwise spring section. This proximal spring section has the highest relative stiffness to account for the moment arm to the distal end of the catheter and enable the smooth, approximately constant radius curvature under lateral load, as seen in FIG. 11E. This section is at least about 2× or 3× or preferably 4× stiffer than the distal end 9. As illustrated, the spring section has 3 revolutions, 0.021" pitch, 0.0045" width.

3. First proximal port. Annular frame is configured to define an oblong port and opposing aperture pair to provide differing visual presentation under fluoroscopy indicative of rotational orientation. Dual exit locations are approximately 180 degrees rotated.

4. 2nd spring region may have a counterclockwise rotation to enhance torque response, and may also have a dual start. As illustrated, the second spring section has 4 revolutions, 0.014" pitch, 0.0040" width.

5. The middle port pair 132 is rotated 60 degrees from first port pair 130. All other geometry of the three port pair frame segments are the same.

6. The third spring region may have about 4 revolutions, 0.014" pitch, 0.0030" width.

7. The distal port pair 134 is rotated 60 degrees from the middle port pair 132.

8. The fourth spring region may be provided with between about three and 10 and in the illustrated embodiment six dual start revolutions, 0.0105" pitch, 0.0030" width.

9. The distal end is provided with a plurality of anchors configured for maximum surface area to allow embedded anchoring within the soft tip material to intertwine with the metallic insert and increase tensile strength.

Any of the pitch and width dimensions provided above can be varied by +/−5%, 10% 15%, or 20% depending upon the desired performance.

Reinforcement of the apertures can be accomplished with multiple components that can articulate. Reinforcement may have spring like components for inter-connection. Material may be polymeric or metallic. Material may be radiopaque. Reinforcement will be layered within polymeric tubing to create a laminate structure. Ports may be cut through the braided regions before or after lamination. Multiple materials of construction may be used. Components may be welded together for robustness. Ports can be singulated (discrete components) and positioned in multiple orientations to optimize selection by the guidewire. Material may be polymeric or metallic. Ports can be single sided. Ports can be dual sided as illustrated.

One aspect of the invention involves aspiration via the side ports to secure adjacent tissue. Aspiration can be accomplished via the guidewire exit ports and/or separate aspiration ports.

Figure 12:
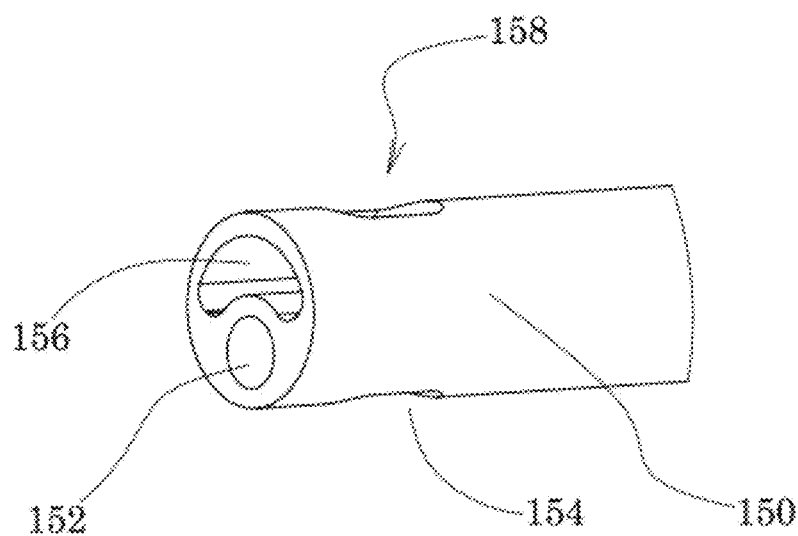
FIG. 12 is a cross sectional perspective view of a catheter shaft portion having separate guide wire and aspiration lumen.

For example, referring to FIG. 12, there is illustrated a perspective cross section through a catheter body segment 150, showing a guidewire lumen 152 in communication with at least one exit port 154, and a separate aspiration lumen 156 in communication with at least one aspiration port 158. In any of the embodiments disclosed herein, the aspiration lumen or guidewire lumen may also be used to infuse fluids which may include one or more drugs.

Figure 13:
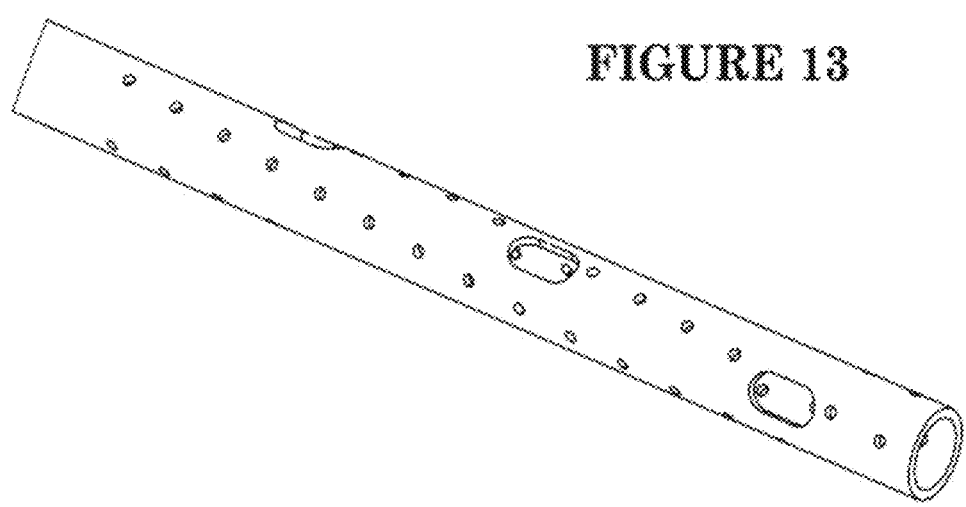
FIG. 13 is a perspective view of a reentry zone having a mix of reentry ports and tissue stabilizing aspiration ports.

FIG. 13 illustrates a reentry catheter segment having relatively larger guidewire exit ports, and a plurality of smaller aspiration ports. Aspiration can be accomplished either via guidewire exit ports or dedicated aspiration ports. In either case, aspiration can reduce the blood volume in the neolumen and or stabilize the wall of the neo lumen (intima) to facilitate puncture by the guidewire to facilitate reentry into the native lumen.

Blood aspiration flow rates or pressure may be controlled via an external vacuum source. Vacuum regulators may be provided to control flow rates, and absolute pressures. Guidewire Re-entry port design may also be used to aspirate blood during access into subintimal space. The vacuum source will be able to measure pressure differentials within the device. The vacuum source may be designed as a stand-alone system or connected to a lab's vacuum source.

Additionally, a pressure pump may be used as a vacuum source. Vacuum can be applied in a multitude of modes that are controlled by a surgeon or automated. Modes such as pulsatile for effective aspiration of hematoma, pulsatile to allow axial advancement while removing hematoma, high pressure or low pressure pulsatile vacuum can be controlled by an automatic valve that pulses at a discrete or variable frequency.

FIG. 14 shows different visualization schemes that may be employed. Preferably, the distal tip has high radiopacity to facilitate visualization. First and second marker bands are preferably positioned at the proximal and distal ends of the reentry zone. In one implementation, the reentry zone may be substantially radiolucent, and the frame surrounding each exit port is radiopaque.

The catheter shaft may be steerable bi-directionally or uni-directionality. The catheter shaft may have the ability to accumulate torque between the handle and the tip. The catheter may have the ability to advance in a way that 'taps' to facilitate tracking—axial extension and compression. All of these characteristics are to facilitate tracking through tortuous anatomy and facilitate traversing the subintimal plane.

Figure 16:
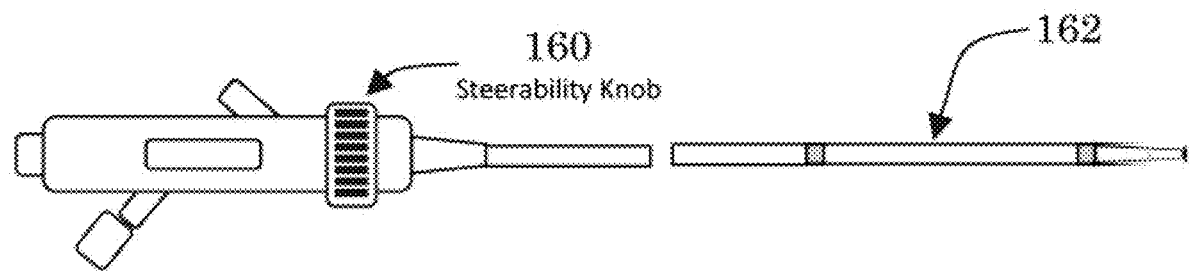
FIG. 16 shows a steerable reentry catheter with integrated handle.

Referring to FIGS. 15 and 16, there is illustrated a bidirectionally steerable catheter 10A. A proximal control 160 such as a rotatable wheel or axial slider is in communication with a distal steering zone 162 by at least one and, as illustrated, two pull wires 164, 166. Manipulation of the control 160 to proximally retract the pull wire 166 will deflect the steering zone 162 in a first direction as illustrated. Proximal retraction of the second pull wire 164 will cause deflection of the steering zone 162 in a second, opposite direction.

Figure 17:
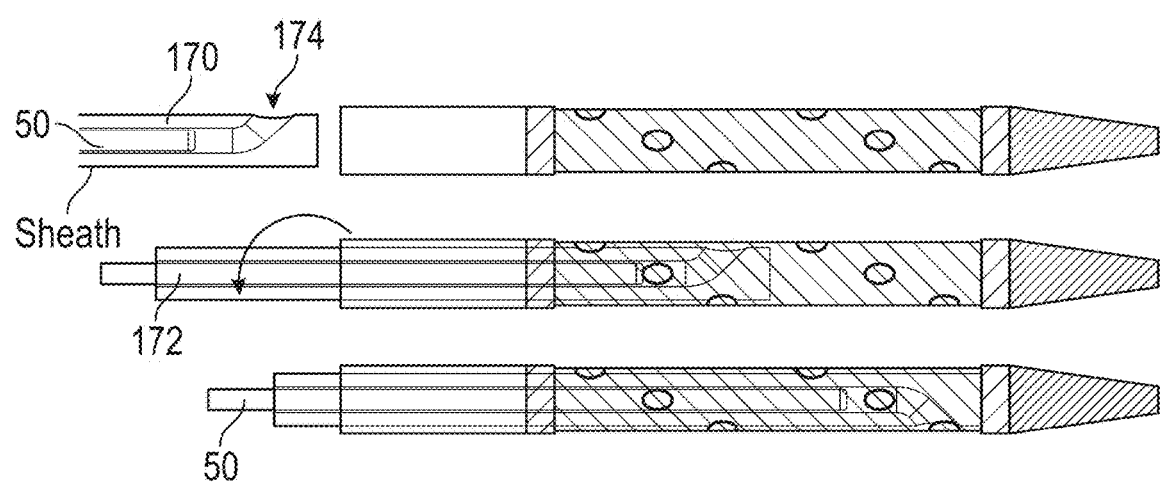
FIG. 17 schematically illustrates reentry zones in combination with a guidewire steering insert.

Referring to FIG. 17, the design may optionally incorporate an internal steerable guide sheath 170 between the guidewire and the catheter shaft. Guide sheath includes a guidewire lumen 172 which terminates distally in a ramped surface to direct a guidewire through a lateral guide wire port 174. To prevent a physician from spinning a GW (trial and error) to get to a desired exit port, the sheath 170 will cover all holes except the desired re-entry port which is aligned with sheath port 174. The user may easily select the desired ports by localizing the ports under fluoroscopy and axially and rotationally adjusting the guide sheath to aim at the desired exit port.

Figure 18:
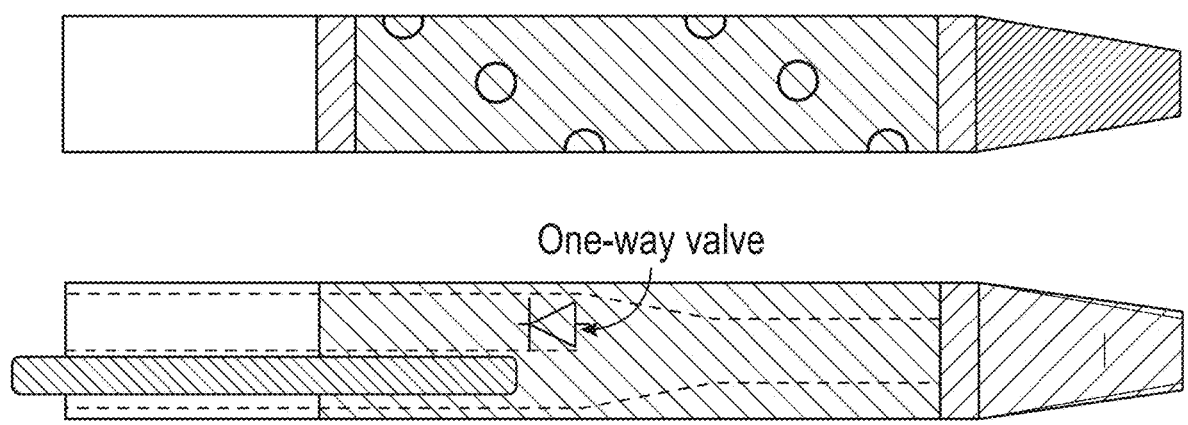
FIG. 18 is a schematic illustration of a reentry catheter distal end having one configuration of a rapid exchange lumen.

Referring to FIG. 18, a dual-lumen catheter shaft may be provided to allow for a Rapid Exchange catheter design. A first, reentry guidewire may be advanced through the lumen accessed vial the proximal luer, and a second, navigational guidewire may be advanced through the second, rapid exchange lumen. In this configuration, the proximal exit port for the second, rapid exchange lumen will be located on a side of the catheter distally of the proximal luer, such as within about 40 cm or 30 cm or 20 cm of the distal end of the catheter.

The first lumen may also be used for aspiration while the second lumen may only be available for a guidewire. It may be desirable to isolate one or more lumens for aspiration, such as shown in FIG. 18. For example a one-way valve may permit passing of a guidewire but also close when the guidewire is removed to facilitate aspiration via the other lumen.

Figure 19:
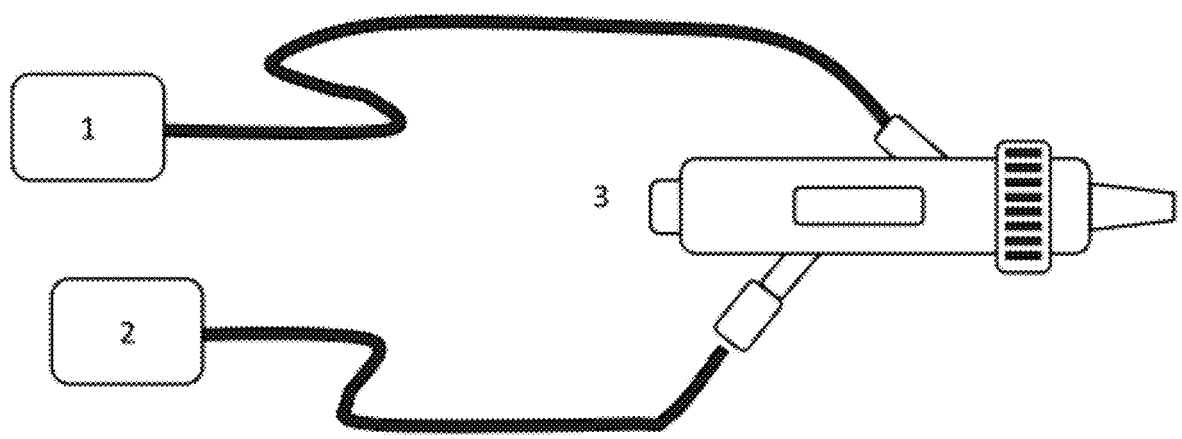
FIG. 19 is a side elevational view of the integrated handle.

Referring to FIG. 19, an integrated handle 3 may be connected to a power source (1) for therapeutic delivery while accessing the subintimal space. Power sources may include, for example, radio frequency generators for RF ablation or cryoablation generators, and a RF or cryo delivery element may be carried by the distal end of the catheter or by a removable catheter insert depending upon the desired functionality.

The integrated handle may also be connected to a vacuum source (2) for blood aspiration to prevent hematoma as well as assisting with device fixation within the subintimal space. The integrated device may include a vacuum accumulator within the handle that could interact with operator controls.

The integrated handle and one or two or more lumen extending throughout the catheter may also be configured to be compatible with a variety of commonly used tools for CTO crossing procedures, including guidewires, guide liners to increase stiffness for increase pushability, drilling microcatheters to gain access to the subintimal space; dilation balloon catheters; or infusion pumps for delivering therapeutic agents.

Figure 20A:
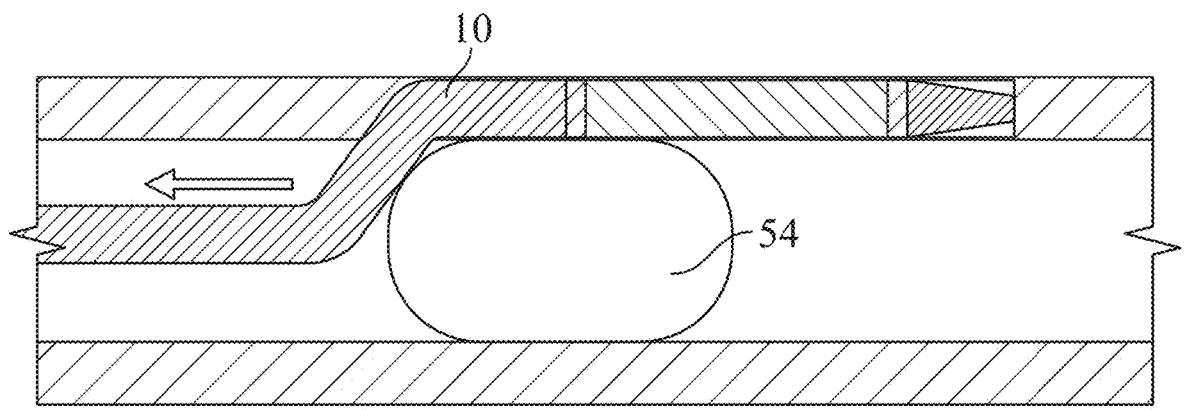
FIGS. 20A-20C illustrate the use of the reentry catheter to accomplish a delivery into the subintimal space.
Figure 20B:
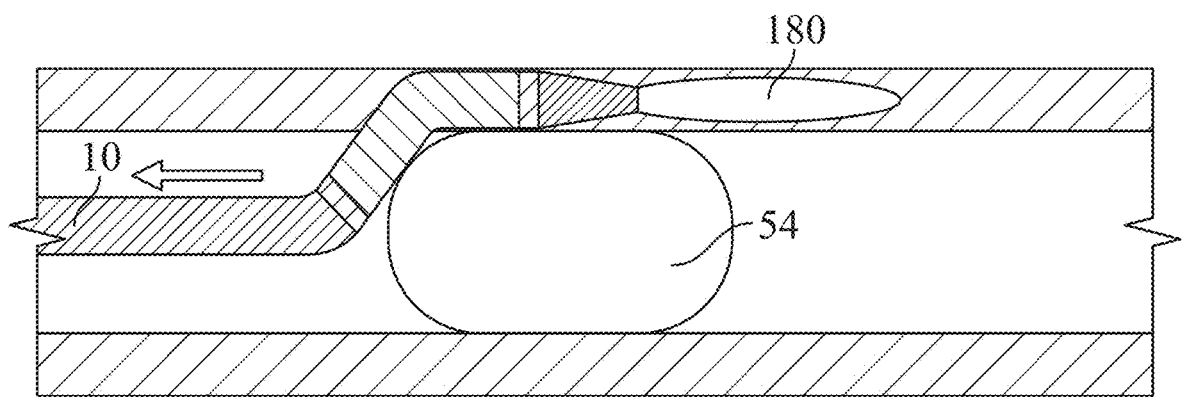
Figure 20C:
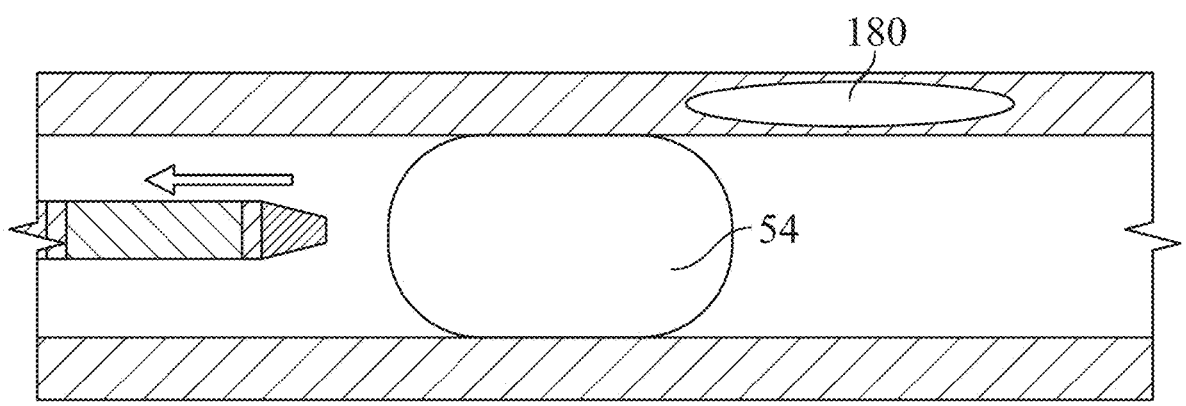

Referring to FIGS. 20A-20C, the catheter 10 provides the ability to access the subintimal space and achieve a variety of additional advantages such as the ability to deliver drugs such as therapeutic agents to help heal dissections, anticoagulants, or contrast, or monitor ECG signals. In addition, the catheter enables delivery of a variety of devices 180, such as customized implants or sensors.

It may be desirable to coat the outside surface of the guidewire and/or the inside surface of the wall defining the guidewire lumen with a lubricous coating to minimize friction as the catheter 10 is axially moved with respect to the guidewire. A variety of coatings may be utilized, such as parylene, Teflon (a brand name for polytetrafluoroethylene (PTFE)), silicone rubber, polyimide-polytetrafluoroethylene composite materials or others known in the art and suitable depending upon the material of the guidewire or inner surface of the tubular wall.

In prior art intravascular catheters, the intended guidewire is normally configured to substantially occupy the guidewire lumen, with a minimal tolerance necessary to avoid excessive friction. For example, a catheter having a 0.018" ID guidewire lumen might be used with a 0.014" guidewire. The reentry guidewire of the present invention is preferably substantially smaller than the ID of the complementary lumen. For example, a 0.014" guidewire may be used with a catheter 10 having a 0.028" lumen. In general, the guidewire will have a diameter that is no more than about 80%, and preferably no more than about 70% or 60% of the ID of the corresponding lumen. This provides an aspiration flow path in the space between the guidewire and the lumen wall to enable aspiration of blood from the intraluminal space and anchoring of the catheter against adjacent tissue while the guidewire remains in place. For example, with a 0.014" guidewire present and a maximum vacuum pressure of 20 mmHg, at least about 6 mL/Min, and preferably at least about 8 mL/MIN or at least about 10 mL/min of saline or water or more is aspirated.

The catheters of the present invention may comprise any of a variety of biologically compatible polymeric resins having suitable characteristics when formed into the tubular catheter body segments. Exemplary materials include polyvinyl chloride, polyethers, polyamides, polyethylenes, polyurethanes, copolymers thereof, and the like. Optionally, the tubular body may further comprise other components, such as radiopaque fillers; colorants; reinforcing materials; reinforcement layers, such as braids and helical reinforcement elements; or the like. In particular, the tubular body may be reinforced such as with an embedded coil or one or two or more braided tubular layers in order to enhance its column strength and torqueability while preferably limiting its wall thickness and outside diameter. The tubular body 16 may be produced in accordance with any of a variety of known techniques for manufacturing interventional catheter bodies, such as by extrusion of appropriate biocompatible polymeric materials.

Radiopaque markers may be provided at least at the distal end 25 and the proximal end of the reentry zone 40. One suitable radiopaque marker comprises a metal band which is fully embedded within the catheter wall. Suitable marker bands can be produced from a variety of materials, including platinum, gold, and tungsten/rhenium alloy.

In many applications, the tubular body 16 is provided with an approximately circular cross-sectional configuration having an external diameter within the range of from about 0.025 inches to about 0.065 inches. In accordance with one embodiment of the invention, the proximal section of tubular body 16 has an external diameter of about 0.042 inches (3.2 f) throughout most of its length. Alternatively, a generally oval or flattened cross-sectional configuration can be provided in a distal zone, as well as other noncircular configurations, depending upon the desired performance.

In a catheter intended for peripheral vascular applications, at least the proximal section of body 16 will typically have an outside diameter within the range of from about 0.039 inches to about 0.110 inches. In coronary vascular applications, the proximal section of body 16 will typically have an outside diameter within the range of from about 0.025 inches to about 0.080 inches. The OD of the catheter may taper or step to a smaller diameter or dimension in a distal zone.

Diameters outside of the preferred ranges may also be used, provided that the functional consequences of the diameter are acceptable for the intended purpose of the catheter. For example, the lower limit of the diameter for any portion of tubular body 16 in a given application will be a function of the number of fluid or other functional lumen contained in the catheter, together with the acceptable minimum performance characteristics.

For example, referring to FIG. 9, a strain relief 182 may extend within the range of from about 25 mm to about 50 mm, or about 35 to about 40 mm from the proximal hub. The OD steps down from about 0.080" to about 0.041" (less than about 75% or 65% or less than about 55% of the OD of the strain relief 182 section of the catheter body) distally of transition 184. The catheter body distally of transition 184 may include at least two or three zones of distinct flexibility. In a modified 3 point bend test, a) a distalmost zone will preferably exert between about 6-10 gf when deflected 15 mm but less than 15 gf. An intermediate or mid shaft zone will preferably exert between about 10-20 gf when deflected 15 mm but less than 30 gf, and a proximal zone will preferably exert between about 30-60 gf when deflected 15 mm but less than 100 gf. Preferably, the catheter shaft will exert at least about 0.10 ozf-in at the metallic insert junction when rotated 360 but less than 1 ozf-in.

The proximal zone may have a length within the range of from about 850-1050 mm, and in some implementations from about 925 to about 975 mm. The intermediate zone may have a length within the range of from about 150 mm to about 250 mm, from about 175 mm to about 225 mm, or about 190 mm to about 210 mm. The distal zone may have a length within the range of from about 150 mm to about 250 mm, from about 180 mm to about 230 mm, or about 195 mm to about 220 mm.

Although the present invention has been described in terms of certain preferred embodiments, it may be incorporated into other embodiments by persons of skill in the art in view of the disclosure herein. The scope of the invention is therefore not intended to be limited by the specific embodiments disclosed herein, but is intended to be defined by the full scope of the following claims.

Further variations and additional details of the catheters disclosed herein are disclosed in the attached Appendix, any one or combination of which may be combined with any of the features described above, depending upon the desired performance. The contents of the Appendix are hereby incorporated by reference in their entirety herein.

What is claimed is:

1. An intravascular catheter comprising:
    an elongate flexible tubular body, having a proximal end, a distal end and a tubular side wall defining at least one lumen extending there through;
    first, second and third opposing pairs of radiopaque rings in the side wall, spaced axially apart from each other;
    wherein a first transverse axis extending through the first pair of rings is rotationally offset within the range of from about 10° to about 60° from a second transverse axis extending through the second pair of rings, and the second transverse axis is rotationally offset within the range of from about 10° to about 60° from a third transverse axis extending through the third pair of rings, further comprising an aperture in the side wall through each ring, wherein the aperture is formed within an eyelet axially separated from an adjacent eyelet by a hinge portion, and wherein an aperture comprises a minor axis and a transverse major axis having a length of at least about 150% of the length of the minor axis.

2. An intravascular catheter as in claim 1, further comprising a frame connecting the rings.

3. An intravascular catheter as in claim 2, wherein portions of the frame axially in between the opposing pairs of rings comprise hinges.

4. An intravascular catheter as in claim 3, wherein each hinge comprises a helical strut.

5. An intravascular catheter as in claim 4, wherein portions comprising the plurality of apertures and intervening hinge portions are a unitary body laser cut from a tube.

6. An intravascular catheter as in claim 2, wherein the rings have a wall thickness of no more than about 0.05 inches.

7. An intravascular catheter as in claim 6, wherein the rings have a wall thickness of no more than about 0.005 inches.

8. A subassembly for integration into the wall of a catheter, comprising:
    a tubular body comprising a plurality of aperture portions and intervening hinge portions, each aperture portion comprising a first and a second aperture carried on opposing sides of the tubular body, wherein a first axis extending transversely through the tubular body and the first and second apertures of a first aperture portion is rotationally offset from a second axis extending transversely through the tubular body and the first and second apertures of a second aperture portion, wherein at least one aperture of the first and a second apertures comprises a minor axis and a transverse major axis having a length of at least about 150% of the length of the minor axis.

9. A subassembly as in claim 8, wherein the intervening hinge portions each comprise a helical strut.

10. A subassembly as in claim 9, wherein the aperture portions and intervening hinge portions are a unitary body laser cut from a tube.

11. A subassembly as in claim 10, wherein the body has a wall thickness of no more than about 0.05 inches.

12. A subassembly as in claim 11, wherein the body has a wall thickness of no more than about 0.005 inches.

13. A subassembly as in claim 8, wherein each aperture is formed within an eyelet separated from an adjacent eyelet by a hinge portion.

14. A subassembly as in claim 8, wherein the plurality of aperture portions comprises at least three aperture portions with intervening hinge portions, and a first hinge portion of the intervening hinge portions comprises a helical strut having a first pitch, and a second hinge portion of the intervening hinge portions spaced apart from the first hinge portion by an aperture portion comprises a helical strut having a second, different pitch.

15. An intravascular catheter with fluoroscopically visible indicium of rotational orientation, comprising:
   an elongate flexible tubular body, having a proximal end, a distal end and a tubular side wall defining at least one lumen extending there through;
   first, second and third opposing pairs of radiopaque rings in the side wall, spaced axially apart from each other,
   wherein a first transverse axis extending through the first pair of rings is rotationally offset within the range of from about 10° to about 60° from a second transverse axis extending through the second pair of rings, and the second transverse axis is rotationally offset within the range of from about 10° to about 60° from a third transverse axis extending through the third pair of rings; and
   further comprising a frame connecting the rings, wherein portions of the frame axially in between the opposing pairs of rings comprise hinges, wherein each hinge comprises a helical strut, and wherein the aperture portions and intervening hinge portions are a unitary body laser cut from a tube.

* * * * *